US006216039B1

(12) United States Patent
Bourgeois

(10) Patent No.: US 6,216,039 B1
(45) Date of Patent: Apr. 10, 2001

(54) METHOD AND APPARATUS FOR TREATING IRREGULAR GASTRIC RHYTHMS

(75) Inventor: Ivan Bourgeois, Verviers (BE)

(73) Assignee: Medtronic Inc., Minneapolis, MN (US)

(*) Notice: Subject to any disclaimer, the term of this patent is extended or adjusted under 35 U.S.C. 154(b) by 0 days.

(21) Appl. No.: 08/850,724

(22) Filed: May 2, 1997

(51) Int. Cl.$^7$ .................................................. A61N 1/365
(52) U.S. Cl. ............................................................ 607/40
(58) Field of Search ............................ 607/40, 41, 73, 607/137, 138, 143; 600/29, 30

(56) References Cited

U.S. PATENT DOCUMENTS

| 4,981,470 | 1/1991 | Bombeck . |
| 5,188,104 | 2/1993 | Wernicke et al. . |
| 5,292,344 | 3/1994 | Douglas . |
| 5,861,014 | * 1/1999 | Familoni ................................ 607/40 |

FOREIGN PATENT DOCUMENTS

| 0571 938A2 | 5/1993 | (DE) . |
| 2 237 648 | 7/1973 | (FR) . |
| 2 453 630 | 4/1979 | (FR) . |
| WO 94/27672 | 5/1994 | (GB) . |
| 1651918A1 | 5/1991 | (SU) . |

OTHER PUBLICATIONS

"High Prevalence of Gastric Electrical Dysrhythmias InDiabetic Gastroparesis"—T.L. Abell et al. (Gastroenterology, 1985; 88:1299).

"Development of a Canine Model for Gastric Pacing"—B. Johnson et al. (Gastroenterology, vol. 98, No. 5, Part 2).

"Postoperative Gastroparesis and Tachygastria—Response to Electric Stimulation and Erythromycin"—M.P. Hocking (Surgery, vol. 114, No. 3, Sep. 1993, pp. 538–542).

"Electrogastrographic Study of Gastric Myoelectrical Activity in Patients with Unexplained Nausea and Vomiting"—H. Geldof et al. (Gut, 1986, vol. 27, pp. 799–808).

"Efficacy of Electrical Stimulation at Frequencies Higher than Basal Rate in Canine Stomach"—B. Familoni et al. (Digestive Diseases and Sciences, vol. 42, No. 5, May 1997, pp. 892–897).

(List continued on next page.)

Primary Examiner—Jeffrey R. Jastrzab
(74) Attorney, Agent, or Firm—Thomas F. Woods; Michael J. Jaro; Harold Patton

(57) ABSTRACT

A method and apparatus for treating gastric arrhythmia. The apparatus features an implantabler pulse generator which may be coupled to the gastric system through one or more medical electrical leads. In the preferred embodiment the leads couple to the circular muscle layer of the stomach. The apparatus further features a sensor to sense slow waves and determines whether the slow waves are occurring in an irregular or unstable manner. The apparatus further permits such slow waves to be diagnosed as either occurring in a bradygastria or a tachygastria and provides the appropriate electrical stimulation in response. Thus the present invention diagnoses and treats irregular gastric rhythm such as bradygastria and tachygastria.

11 Claims, 13 Drawing Sheets

OTHER PUBLICATIONS

"Analysis of Gastric Emptying Data"—J.D. Elashoff et al (Gastroenterology 1982: 83:pp. 1306–1312).

"Gastric Myoelectric Activity in Patients with Chronic Idiopathic Gastroparesis"—M. Bortolotti et al. (Gastrointestinal Motility, vol. 2, No. 2, Jun. 1990, pp. 104–108).

GastricElectromechanical and Neurohormonal Function in Anorexia Nervosa:—T.L. Abell et al. (Gastroenterology, Nov. 1987:93:pp. 958–965).

Electrogastrography—Current Assessment and Future Perspectives—T.L. Abell et al. (Digestive Diseases and Sciences, vol. 33, No. 8, Aug. 1988, pp. 982–992).

Electrogastrographic Study of Patients with Unexplained Nausea, Bloating and Vomiting—C.H. You et al. (Gastroenterology, vol. 79, No. 2, Aug. 1980, pp. 311–314).

"Motility of the Stomach and Gastroduodenal Junction"—K.A. Kelly (Physiology of the Gastrointestinal Tract, 1981, pp. 393–410).

"Gastric Dysrhythmias and Nausea of Pregnancy"—K.L. Koch et al. (Digestive Diseases and Science, vol. 35, No. 8, Aug. 1990, pp. 961–968).

Ergebnisse der Inneren Medizin und Kinderheilkunde—16:198 (1961) (cover page).

Electric Stimulation of the Gastrointestinal Tract—GP Apr. 1994.

Gastrointestinal Pacing—A New Concept in the Treatment of Ileus—Biomedical Sciences Instrumentation vol. 1. 1963 (A.M. Bilgutay, R. Wingrove, W.O. Griffen, R.C. Bonnabeau and C.W. Lillehei).

Gastro–intestinal Pacing: Will It Work?—American Journal of Surgery, Feb. 1966 (J. Sonneland).

Evaluation of the Intrinsic Innervation of the Internal Anal Sphincter using Electrical Stimulation—Gut, 1989, 30, 935–938 (M.A. Kamm, J.E. Lennard–Jones, and R.J. Nicholls).

Enhancing Absorption in the Canine Short Bowel Syndrome by Intestinal Pacing—Surgery, Aug. 1980 (H.E. Gladen and K.A. Kelly).

Pacing the Human Stomach—Surgery, Feb. 1992 (B.W. Miedema, M.G. Sarr and K.A. Kelly).

Ectopic Jejunal Pacemakers and Gastric Emptying after Roux Gastrectomy: Effect of Intestinal Pacing—Surgery, Nov. 1989 (L.Karlstrom and K.A. Kelly).

A New Treatment for Rectal Prolapse (Abridged)—Proceedings of the Royal Society of Medicine (K.P.S. Caldwell).

Prognosis of Patients with and Ileastomy—Section of Proctology (A.G. Parks).

Differential Responses of the Canine Gastric Corpus and Antrum to Electric Stimulation—American Journal of Physiology, Jan. 1974 (K.A. Kelly).

The Electrical Control of Sphincter Incompetence—The Lancet, Jul. 23, 1963 (K.P.S. Caldwell).

Gastric Motor Physiology and Pathophysiology—Surgical Clinics of North America, vol. 73, Dec. 1993 (J.J. Cullen and K.A. Kelly).

The Role of the Extrinsic Antral Nerves in the Regulation of Gastric Emptying—Surgery, Gynecology & Obstetrics, Sep. 1977, vol. 145 (C.T. Mroz and K.A. Kelly).

A New Treatment for Rectal Prolapse—Geriatrics, Jan. 1968 (K.P.S. Caldwell).

Incontinence—Transactions of The Medical Society of London, Ordinary Meeting, Apr., 1973 (K.P.S. Caldwell).

The Treatment of Incontinence—Hospital Management (K.P.S. Caldwell).

Control of Gastro–intestinal Motility with Electrical Pacing—Jap. J. Smooth Muscle Res. 21: Suppl., 125, 1985 (H.M. Richter, III, S. Bjorck and K.A. Kelly).

Effect of Electrical Stimulation on Gastric Electrical Activity, Motility and Emptying—Neurogastroenterology and Motility 1995 (J.C. Eagon and K.A. Kelly).

Independence of Canine Gastric and Duodenal Pacesetter Potentials Shown by Electric Pacing—May Clin. Proc, Jan. 1977, vol. 52 (H.E. Gladen and K.A. Kelly).

Duodenal–Gastric Refulx and Slowed Gastric Emptying by Electrical Pacing of the Canine Duodenal Pacesetter Potential—Gastroenterology 72:429–433, Mar. 1977 (K.A. Kelly and C.F. Code).

Pacing the Human Gut—The American Journal of Gastroenterology, vol. 89, No. 3, 1994 (D.A. Johnson and E.L. Cattau).

Pacing the Gut—Gastroenterology, Dec. 1992 (K.A. Kelly).

Human Gastric Myoelectric Activity and Gastric Emptying Following Gastric Surgery and With Pacing—1992 Gastroenterological (M.P. Hocking, S.B. Vogel and C.A. Sninsky).

Pacing the Canine Stomach with Electric Stimulation—American Journal of Physiology, Mar. 1972 (K.A. Kelly and R.C. La Force).

Gastric Emptying of Liquids and Solids: Roles of Proximal and Distal Stomach—Editorial Review, The American Physiological Society 1980 (K.A. Kelly).

Electric Pacing of Intact and Transected Canine Small Intestine and its Computer Model–13 American Journal of Physiology, vol. 229, Nov. 1975 (O.E. Akwari, K.A. Kelly, J.H. Steinbach and C.F. Code).

Electrical Treatment of Anal Incontinence—The Lancet, Feb. 5, 1966 (B.R. Hopkinson, R. Lightwood).

Electrophysiology of Human Colon Motility in Health and Disease—Clinics in Gastroenterology, vol. 15, No. 4, Oct. 1986 (J.D. Huizinga).

Cerebral Evoked Potentials After Rectal Stimulation—Electroencephalography and Clinical Neurophysiology, 80 (1991) 490–495 (V. Loening–Baucke, N.W. Read and T. Yamada).

Measurement of Gastric and Small Bowel Electrical Activity at Laparoscopy—Journal of Laparoendoscopic Surgery, vol. 4, No. 5, 1994 (B.O. Familoni, T.L. Abell and G. Voeller).

Electrical Stimulation of the Bowel—Arch Surg. vol. 91, Sep. 1965 (J.M. Moran and D.C. Nabseth).

Electrical Pacing for Short Bowel Syndrome—Surgery, Gynecology & Obstetrics—Nov. 1981, vol. 153 (H.E. Gladen and K.A. Kelly).

The Treatment of Incontinence by Electronic Implants—Annals of The Royal College of Surgeons of England, Dec. 1967 (K.P.S. Caldwell).

The Future of Intestinal Pacing—Gastroenterology Clinics of North America, vol. 23, No. 2, Jun. 1994 (J.J. Cullen and K.A. Kelly).

Control of Muscle Tone in the Human Colon—Gut, 1992, 33, 541–546 (C.J. Steadman, S.F. Phillips, M. Camilleri, N.J. Talley, A. Haddad, R. Hanson).

Enhancing the Anti–Dumping Effect of Roux Gastrojejunostomy with Intestinal Pacing—Ann. Surgery, Oct. 1983, vol. 198 (B. Cranley, K.A. Kelly, V.L.W. Go, L.A. McNichols).

The Roux Operation for Postgastrectomy Syndromes—The American Journal of Surgery, vol. 161, Feb. 1991 (B.W. Miedema, K.A. Kelly).

Effect of Duodenal Cooling on Small Intestinal Pacing—Mayo Clin. Proc. Aug. 1982, vol. 57 (K.R. Berg, H.E. Gladen, K.A. Kelly).

Achieving Enteric Continence: Principles and Applications—Mayo Clin Proc. Jul. 1986, vol. 61 (J.H. Pemberton, K.A. Kelly).

Electrical Stimulation of the Human Stomach—Digestive Diseases and Sciences, vol. 30, No. 8, Aug. 1985 (W.E. Waterfall, D. Miller, D.N. Ghista).

Gastric Electrical Stimulation as a Possible New Therapy for Patients with Severe Gastric Stasis—Gastroenterology, vol. 100, No. 5, Part 2 (T.L. Courtney, B.D. Schirmer, B.E. Ballahsene, O.L. Updike and R.W. McCallum).

Temporary and Permanent Electrical Stimulation of the Human Stomach Using High Frequency Pacing—Motility and Nerve–Gut Interactions, Apr. 1993 (B.O. Familoni, T.L. Abell, G. Voeller, A. Salem, O. Gaber, D. Nemoto).

Long–Term Electrical Stimulation of the Human Stomach—Gastroenterology, vol. 106, No. 4, Part 2 (B.O. Familoni, T.L. Abell, G. Voeller, A. Salem, O. Gaber, D. Nemoto).

A Model of Gastric Electrical Activity in Health and Disease—IEEE Transactions on Biomedical Engineering, vol. 42, No. 7, Jul. 1995 (B.O. Familoni, T.L. Abell, K.L. Bowes).

Use of Spectral Analysis in the Detection of Frequencey Differences in the Electrogastrograms of Normal and Diabetic Subjects—IEEE Transactions on Biomedical Engineering, vol. 35, No. 11, Nov. 1988 (C.J. Pfister, J.W. Hamilton, N. Nagel, P. Bass, J.G. Webster and W.J. Tompkins).

Gastric Motility after Gastric Operations—Surgery Annual 1974 (K.A. Kelly).

Electrical Stimulation of Gastric Electrical Control Activity—American Journal of Physiology, vol. 225, No. 1, Jul. 1973 (S.K. Sarna and E.E. Daniel).

Electrical Pacing of the Roux Limb Resolves Delayed Gastric Emptying—Journal of Surgical Research 42, 635–641 (1987) (A. Sawchuk, D. Canal, J.L. Grosfeld, <. Slaughter, G. Gardner, T. O'Connor and D. Behrman).

Gastrointestinal Pacing—Staff Report Meeting—University of Minnesota Medical Bulletin 1965 (A.M. Bilgutay, R. Wingrove, W.O. Griffen, A. Nakib, R.C. Bonnabeau, C.W. Lillehei).

Acceleration of Gastric Emptying with Electrical Stimulation in a Canine Model of Gastroparesis—1992 the American Physiology Society (B–E Bellahséne, C.D. Lind, B.S. Schirmer, O.L. Updike and R.W. McCallum).

A Trial of a Gastro–intestinal Pacemaker—Journal of the Irish Medical Association Jan. 1966 (P.N. Fitzpatrick, and A.W. Chen).

Behavioral and Gastrointestinal Changes (Motility and Blood Flow) Induced by Electrical Stimulation of the Lateral Hypothalamus in Cats—Abstr. XI Scand. Physiol. Congr. Copenmhagen 1963, Suppl. No. 213 (F. Björn and E.H. Rubinstein).

Gastrointestinal Pacemaker—The Lancet, Dec. 7, 1963 (J.M. Sanchez).

Gastrointestinal Pacing—Modern Medicine, Mar. 15, 1965 (A.M. Bilgutay, R. Wingrove, W.O. Griffen, A. Nakib, R.C. Bonnabeau and C.W. Lillehei).

Response to Gastrointestinal Pacing: Antral, Duodenal and Jejunal Motility in Control and Postoperative Patients—Annals of Surgery, Jul. 1966 (T. Berger, J. Kewenter, N.G. Kock).

Evaluation of a Portable Gastric Stimulator—IEEE/9th Annual Conference of the Engineering in Medicine and Biology Society, 1987 (B–E. Bellahsene, R.W. McCallum, O.T. Updike).

Role of Gastric Pacesetter Potential Defined by Electrical Pacing—Canadian Journal of Physiology and Pharmacology, vol. 50, Oct. 1972 (K.A. Kelly and R.C. La Force).

The Endomotorsonde—A New Device for Studying the Gastrointestinal Tract—The American Journal of Medical Electronics, Jul.–Sep. 1964 (J.P.M. D'Haens).

Electronic Pacemakers of the Heart, Gastrointestinal Tract, Phrenic Nerve, Bladder and Carotid Sinus: Current Status—Surgery, Aug. 1966, vol. 60, No. 2 (C.E. Anagnostopoulos, W.W.L. Glenn).

Control of Postoperative Adynamic Bowel in Dogs by Electric Stimulation—vol. IX Trans. Amer. Soc. Artif. Int. Organs, 1963 (D. R. de Villiers, I. Saltiel, A. Nonoyama and A. Kantrowitz).

Reverse Electrical Pacing Improves Intestinal Absorption and Transit Time—Surgery, vol. 100, No. 2, Aug. 1986 (A. Sawchuk, W. Nogami, S. Goto, J. Yount, J.A. Grosfeld, J. Lohmuller, M.D. Grosfeld and J.L Grosfeld).

External Stimulation of Gastric Antrum and Gastric Secretion—The American Journal of Gastroenterology, vol. 52, No. 6, Dec. 1969 (P. Lott, T. Geisel, N.C. Jefferson and H. Necheles).

Electrical Activity of the Gastric Antrum in Normal Human Subjects—The American Journal of Digestive Diseases, vol. 16, No. 7, Jul. 1971 (H. Monges and J. Salducci).

Gastric Pacemakers—Gastroenterology vol. 70, No. 2, Feb. 1976 (S.K. Sarna, K.L. Bowes and E.E. Daniel).

Apparatus for Electrical Stimulation of Weakened Peristaltic Activity of the Stomach (Experimental Investigation)—Biomedical Eng. Mar.–Apr. 1973 (M.A. Sobakin and V.A. Shepelev).

Clinical Evaluation of the Gastrointestinal Pacer—Surgery, Gynecology & Obstetrics, Jan. 1965 (D.C. Quast, A.C. Beall and M.E. DeBakey).

Electrostimulation of the Small and the Large Bowel in Dogs—Biomedical Sciences Instrumentation, May, 1969 (G. Járos and C.R Jansen).

Clinical Experience in Control of Postoperative Adynamic Ileus by Electric Stimulation—Surgical Forum, Vo..14, 1963 (D.R. de Villiers, I. Saltiel, A. Nonoyama and A. Kantrowitz).

Electric Treatment of Intestinal Obstruction and Postoperative Paralysis of the Bowel—Journ. A.M.A., Apr. 1, 1911 (W.H. Dieffenbach).

Studies in Electrical Stimulation of the Adynamic Bowel—The American Journal of Gastroenterology, vol. 44, 1965 (A. Kantrowitz).

Electrical Activity of the Gastrointestinal Tract as an Indication of Mechanical Activity—American Journal of Digestive Diseases, vol. 8, 1963 (E.E. Daniel and K.M. Chapman).

Relative Electrical Impedance as Index of Intestinal Viability—Archives of Surgery, vol. 89, Jul. 1964 (L.C. Carey, K. Kayser, E.H. Ellison and D. Lepley).

Controlled Radiological Evaluation of an Intestinal Pacemaker (Peristart)—Scand. J. Gastroent., 1966, vol. 1 (P. Bach–Nielsen, H. Baden and A.M. Christensen).

An Improved Method for Recording and Analyzing the Electrical Activity of the Human Stomach—IEEE Transactions on Biomedical Engineering, vol. 32, No. 11, Nov. 1985 (B.E. Bellahsene, J.W. Hamilton, J.G. Webster, P. Bass and M. Reichelderfer).

Study of Transcutaneous and Intraluminal Measurement of Gastric Electrical Activity in Humans—Medical & Biological Engineering & Computing, Jul. 1987 (B.O. Familoni, Y.J. Kingma and K.L. Bowes).

Human Gastric Myoelectric Activity and Gastric Emptying Following Gastric Surgery and With Pacing—Gastroenterology, 1992, vol. 103, No. 6 (M.P. Hocking, S.B. Vogel and C.A. Sninsky).

Programmer Medtronic 7432 and Memory Mod 7455—Clinical Plan Gastroparesis, Mar. 2, 1994.

Electrical Pacing of the Stomach in Dogs—IEEE, Sep. 1992 (B.O. Familoni, T.L. Abell).

Gastroparesis and the Current Use of Prokinetic Drugs—The Gastroenterologist, vol. 1, No. 2, Jun. 1993 (B.J. Kendall and R.W. McCallum).

Physiology of the Colon and Rectum—The American Journal of Surgery, vol. 117, Jun. 1969 (R.D. Williams and J.W. Dickey).

Effects of Gastric Pacing on Canine Gastric Motility and Emptying—American Journal of Physiology, vol. 265, No. 4, Oct. 1993 (J.C. Eagon and K.A. Kelly).

Manometric Evaluation of Children with Chronic Constipation Using a Suction Stimulating Electrode—Eur. J. Pediatr. Surg. 2 (1992)287–290 (M. Kubota, A. Nagasaki and K. Sumitomo).

* cited by examiner

METHOD AND APPARATUS FOR TREATING IRREGULAR GASTRIC RHYTHMS

FIELD OF THE INVENTION

This invention relates generally to implanted medical devices and, more particularly, relates to a method and apparatus for use in treating irregular gastric rhythms.

BACKGROUND OF THE INVENTION

The gastrointestinal system includes the stomach, small intestine and large intestine. Like other organs of the body, most notably the heart, these organs naturally undergo regular rhythmic contractions. In particular these contractions take the form of peristaltic contractions and are essential for the movement of food through each of the respective organs. Like the heart, these contractions are the result of regular rhythmic electrical depolarizations of the underlying tissue. With regards to the small intestine and large intestine, normal electrical depolaraziations ("slow waves") typically occur at a rate of approximately 15 and 1 beats per minute (bpm) respectively. Similarly, in the stomach, normal slow waves typically occur at a rate approximately 3 bpm. Not all of these depolaraziations, however, normally result in a contraction of the organ. Rather contractions occur upon the occurrence of a normal electrical depolaraziations followed by a series of high frequency spike activity.

In some individuals, however, either the regular rhythmic peristaltic contractions do not occur or the regular rhythmic electrical depolaraziations do not occur or both do not occur. In each of these situations the movement of food may be seriously inhibited or even disabled. Such a condition is often called "gastroparesis" when it occurs in the stomach. Gastroparesis is a chronic gastric motility disorder in which there is delayed gastric emptying of solids or liquids or both. Symptoms of gastroparesis may range from early satiety and nausea in mild cases to chronic vomiting, dehydration, and nutritional compromise in severe cases. Similar motility disorders occur in the other organs of the gastrointestinal tract ("GI tract"), although by different names.

Diagnosis of gastroparesis is based on-demonstration of delayed gastric emptying of a radio-labeled solid meal in the absence of mechanical obstruction. Gastroparesis may occur for a number of reasons. Approximately one third of patients with gastroparesis, however, have no identifiable underlying cause (often called idiopathic gastroparesis). Management of gastroparesis involves four areas: (1) prokinetic drugs, (2) antiemetic drugs, (3) nutritional support, and (4) surgical therapy (in a very small subset of patients.) Gastroparesis is often a chronic, relapsing condition; 80% of patients require maintenance antiemetic and prokinetic therapy and 20% require long-term nutritional supplementation. Other maladies such as tachygastria or bradygastria can also hinder coordinated muscular motor activity of the GI tract, possibly resulting in either stasis or nausea or vomiting or a combination thereof.

The undesired effect of these conditions is a reduced ability or complete failure to efficiently propel intestinal contents down the digestive tract. This results in malassimilation of liquid or food by the absorbing mucosa of the intestinal tract. If this condition is not corrected, malnutrition or even starvation may occur. Moreover nausea or vomiting or both may also occur. Whereas some of these disease states can be corrected by medication or by simple surgery, in most cases treatment with drugs is not adequately effective, and surgery often has intolerable physiologic effects on the body.

Presently, however, there is no practically effective device or system to intelligently stimulate. Therefore, there is a need in the art for a system and method to properly stimulate the GI tract to thereby treat ineffective or absent electrical muscular activity of the GI tract.

SUMMARY OF THE INVENTION

Thus it is an object of the present invention to provide a method and apparatus to treat gastric arrhythmia, as occurs in patients with gastroparesis.

It is a further object of the present invention to provide a method and apparatus which treats gastric arrythmias with electrical stimulation.

It is a still further object of the present invention to provide a method and apparatus which treats gastric arrythmias by sensing the underlying gastric rhythm, determining whether it is an arrhythmia, and provides the appropriate electrical stimulation to the sensed arrhythmia.

The above and other objects are met by the present invention which is a method and apparatus for treating gastric arrhythmia. The apparatus features an implantable pulse generator which may be coupled to the gastric system through one or more medical electrical leads. In the preferred embodiment the leads couple to the circular muscle layer of the stomach. The apparatus further features a sensor to sense slow waves and determines whether the slow waves are occurring in an irregular or unstable manner. The apparatus further permits such slow waves to be diagnosed as either occurring in a bradygastria or a tachygastria and provides the appropriate electrical stimulation in response. Thus the present invention diagnoses and treats irregular gastric rhythm such as bradygastria and tachygastria.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein.

The FIGS. are not necessarily to scale.

DETAILED DESCRIPTION OF THE INVENTION

Figure 1:
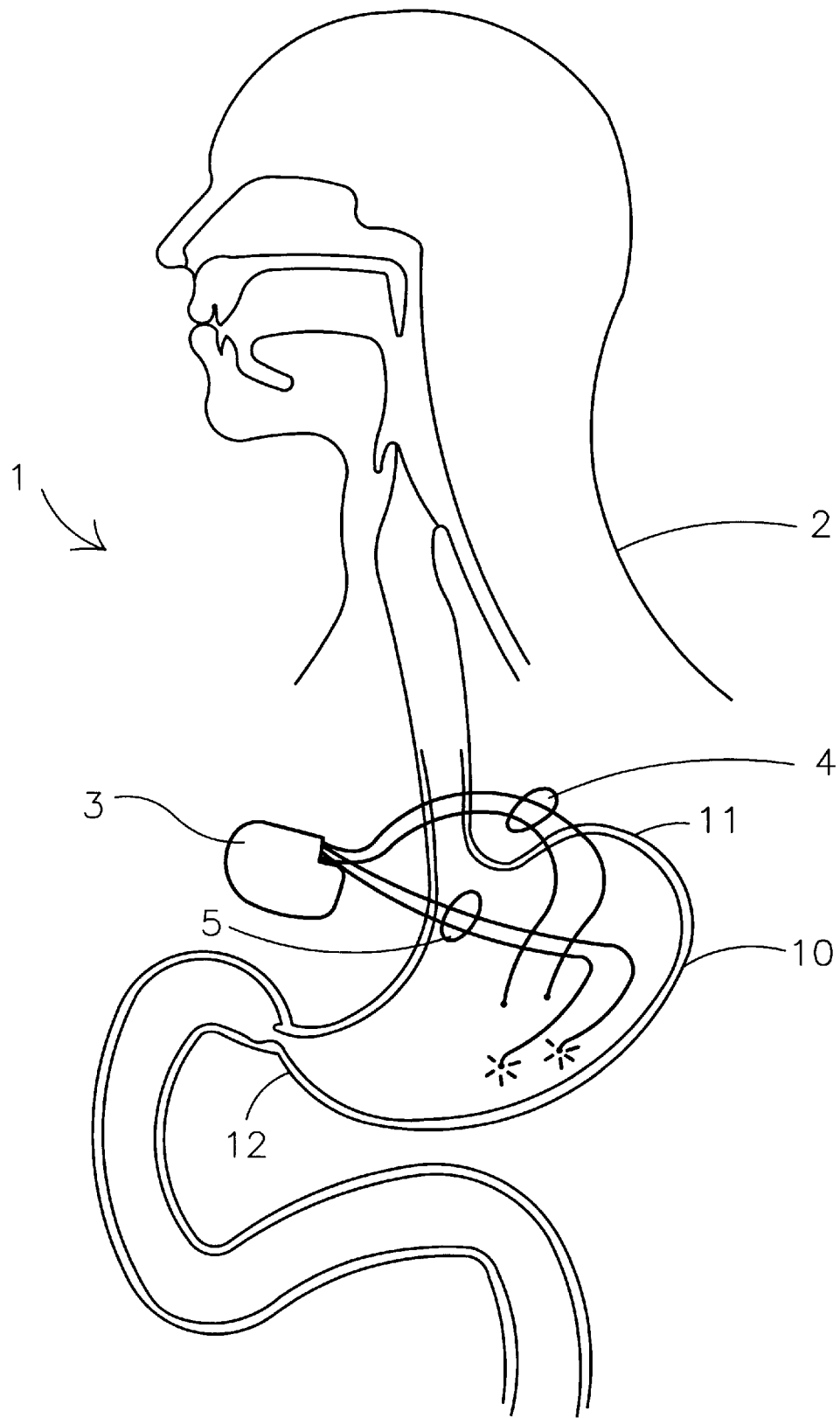
FIG. 1 depicts the apparatus implanted within a patient.

FIG. 1 shows a system 1 implanted in a patient 2. As seen, the system 1 comprises an implantable pulse generator 3 featuring two sets of leads 4, 5 which are coupled to the stomach 10. The first set of leads 4 provide stimulation to the stomach. The second set of leads 5 provide sensing of the gastroelectrical activity of the stomach 10 to the pulse generator 3. In the preferred embodiment, the pulse generator 3 is implanted within the patient 2. As such, the implantable pulse generator 3 features a hermetic enclosure, as is well known in the art. The leads used for both the first set 4 and the second set 5 may be any acceptable lead. In the preferred embodiment, the preferred leads are Medtronic Model No. 4300 intramuscular lead. Of course, other configurations of leads or lead systems may be used, including the use of from only a single lead, a single set of leads (i.e. two), or even the use of three or more sets of leads. Moreover, although shown as being coupled to the stomach it must be understood the present invention may be used along or on any of the other structures and organs along the gastrointestinal tract, including the colon, small intestine, stomach or even the esophagus.

The first set of leads 4 are stimulation leads which conduct stimulation pulses from the pulse generator 3 to the stomach 10. First set of leads 4 are preferably implanted through the serosa at the area within the transition of the corpus and the antrum on the great curvature. Of course, other locations for first set of leads 4 may be used, such as in the fundus, caudud corpus as well as the orad or terminal antrum. The second set of leads 5 are sensing leads which conduct any gastroelectrical activities sensed in the stomach 10 to the pulse generator 3. Preferably the second set of leads 5 are positioned distally in the mid antrum also along the great curvature, although these leads may also be positioned in other locations.

Figure 2:
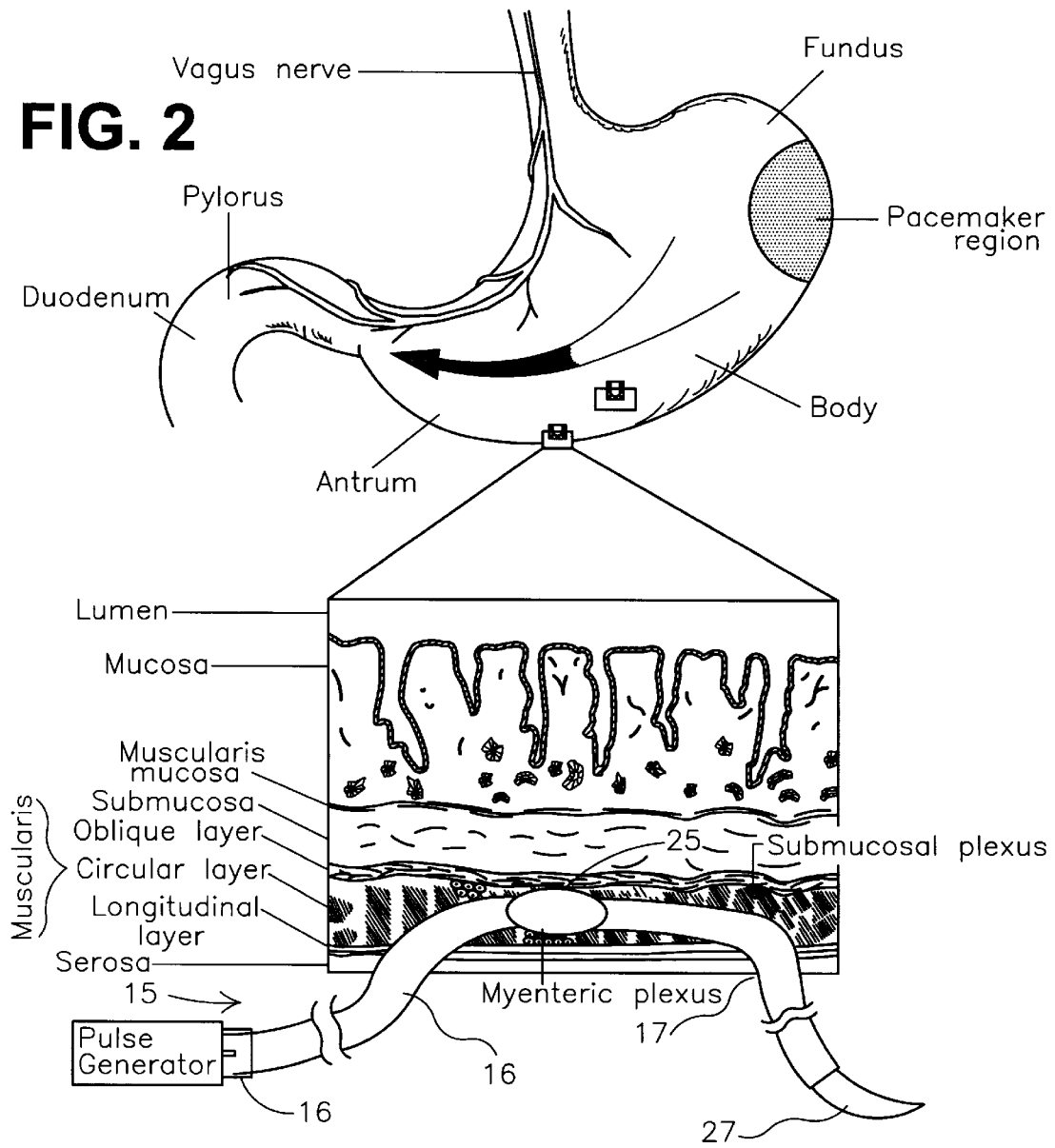
FIG. 2 depicts a detailed view of the stomach muscle showing the electrode of the lead implanted.

FIG. 2 details the preferred positioning of an electrode of a lead within the various layers of the stomach. As seen, the stomach 10 has essentially seven layers of tissue. In the preferred embodiment, the electrode of each lead is positioned into the layers of the stomach muscle as shown. That is, the electrode is positioned such that it intersects both the longitudinal and circular layers. This is believed important by the inventor because in such a manner the electrode is able to also intersect the enteric nervous system of the stomach and be in close contact with the cells of Cajal.

This is believed important as research has shown that intramuscular electrodes may effectively stimulate the stomach with less than one one-thousandths of the energy required for serosal electrodes. Of course, other types of electrodes or lead systems may be used, including those which contact only any one of each of the layers of the stomach organ, such as only the mucosa or only the serosa. Moreover, although in the preferred embodiment a pair of unipolar leads are used for stimulation and a second pair of unipolar leads are used for stimulation, other configurations of leads may be used, such as bipolar, tripolar, quadrapolar, as well as any other configuration suitable such as a unipolar lead and can.

Figure 3:
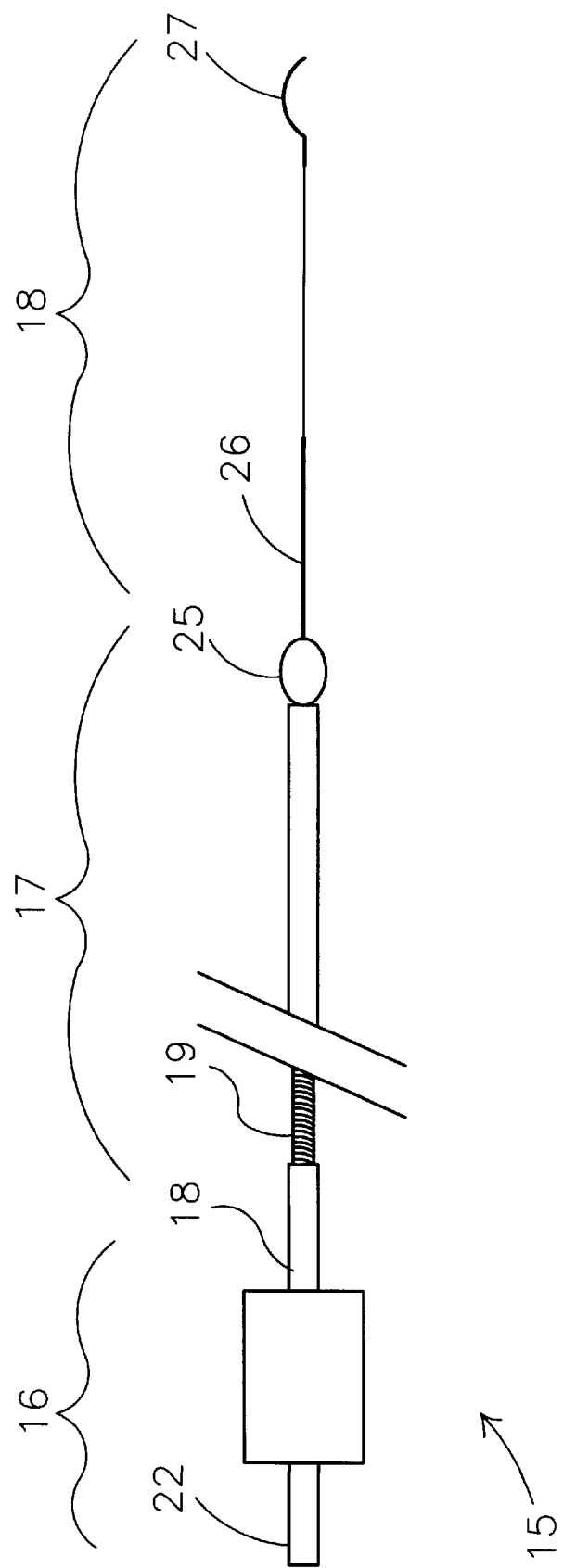
FIG. 3 depicts a plan view of a lead used with the apparatus.

FIG. 3 depicts a plan view of the preferred embodiment lead 15 used in the present invention. As seen, the lead 15 essentially has three sections, connector section 16, body section 17 and fixation section 18. Connector section 16 includes a connector pin 22 to electrically couple the lead 15 into the pulse generator. Any connector pin 22 as well known in the art may be used. Body section 17 includes an electrical conductor 19 surrounded by an electrical insulator 20. In the preferred embodiment electrical conductor 19 is a platinum iridium alloy and electrical insulator 18 is silicone. Of course, other biocompatible materials may also be used. As seen, at the distal end of the body section 17 is an electrode 25. In the preferred embodiment, electrode 25 is a polished platinum iridium alloy. Of course, other materials may likewise be used, such as a porous platinized structure. In addition, the electrode 25 could further feature various pharmaceutical agents, such as dexamethasone sodium phosphate or beclomethasone phosphate in order to minimize the inflammatory response of the tissue to the implanted lead 15. Other agents such as antibiotics may also be used. Located distal to the electrode 25 is the fixation section 18. As seen, fixation section 18 has essentially two piece parts, a suture 26 which is in turn coupled to a needle 27. Needle 27 is preferably curved. In an alternate embodiment suture may feature a fixation coil as is well known in the art to cooperate with the body tissue after implantation to maintain the lead 15 in the position implanted. Of course, other fixation mechanisms may be used, such as fixation discs, as is well known in the art.

Figure 4:
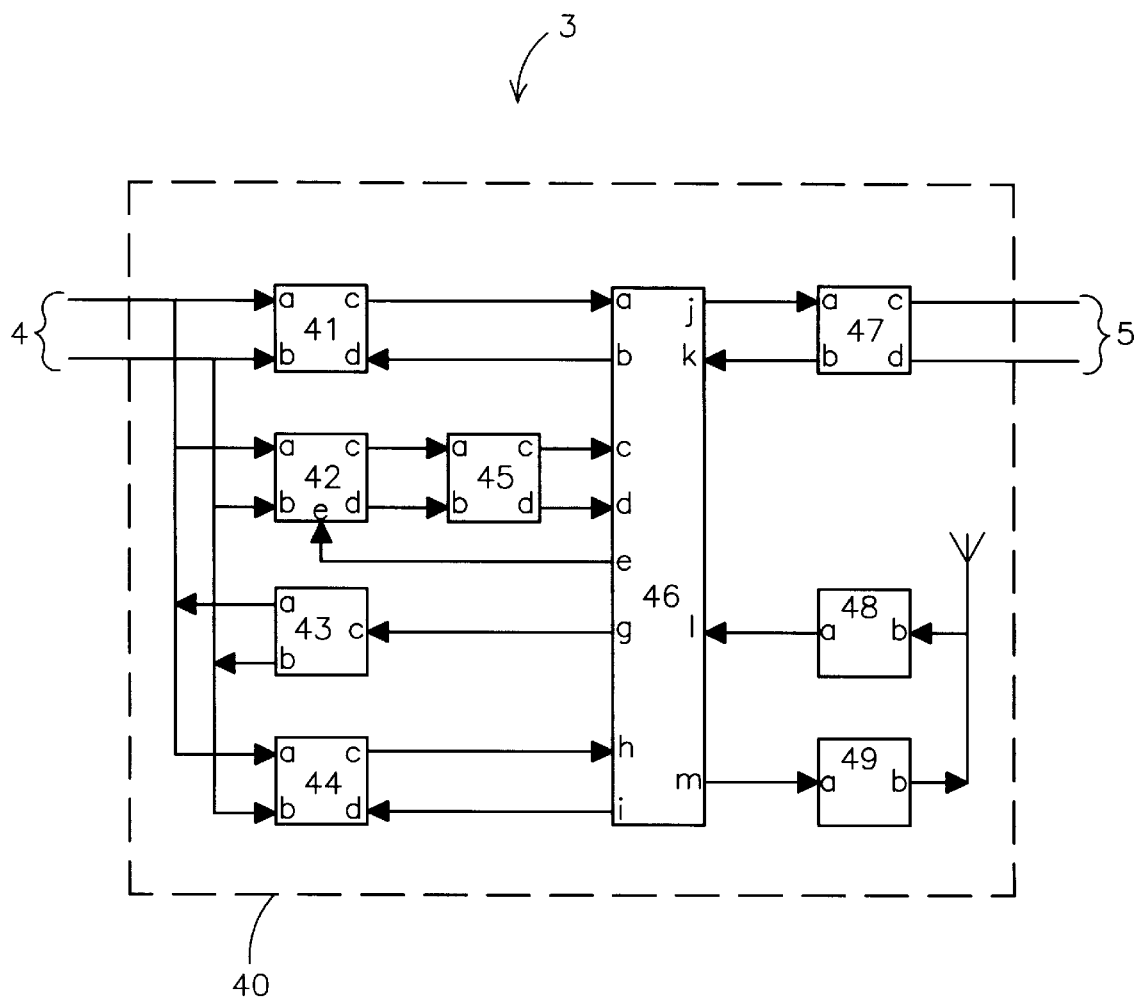
FIG. 4 is a functional block diagram of the pulse generator.

FIG. 4 depicts a functional block diagram of the gastrointestinal pulse generator according to the present invention. As seen, pulse generator 3 is enclosed by hermetic enclosure 40 to the electronics and battery while the device is implanted. Hermetic enclosure may consist of any suitable construction. Pulse generator 3 couples with two sets of leads 4, 5 which are, in turn, coupled to the stomach 10. The first set of leads 4 transmits stimulation pulses from pulse generator 3 to the stomach. The second set of leads 5 provide sensing of the gastroelectrical activity of the stomach 10 to the pulse generator 3. Although in the preferred embodiment the stimulating leads and sensing leads are separate leads, the present invention may also be employed using a combination of lead which both sense and stimulate.

As seen, the sensing leads 4 are coupled into a slow wave detection circuit 41. Slow wave detection circuit 41 includes a band pass amplifier, a slew rate converter and two threshold detectors. Essentially, such a slow wave detection circuit 41 is similar to those used in a cardiac pacemaker but with several important characteristics. First, the band pass amplifier has a much lower center frequency, preferably on the order of 0.3 HZ when used in the stomach. Of course, the present invention may be used in each of the various organs along the GI tract so that the center frequency may be varied accordingly. The slew rate converter operates in a manner well known in the art and generates a signal corresponding to the slew rate of the sensed electrogastrogram. The threshold detectors operates in a manner well known in the art and generate output signals when the sensed input signal is above a threshold level. One threshold detector corresponds to the peak to peak amplitude of the sensed electrogastrogram. The second threshold detector corresponds to the sensed slew rate.

Preferably, the slow wave detection circuit 41 must be able to detect input signals between approximately 30 microvolts and 10 millivolts which have a slew rate between 100 microvolts per/second up to 10 volts per/second with a typical value of 100 millivolts per second. Such a range may be achieved using multiple steps which are controlled by the microprocessor 46 via the input line 46b–41d. To detect the slow wave, both threshold detectors should be coupled using a logical AND configuration. Thus, a signal should then be sent via the output line 41c–46a to the microprocessor 46. The slew rate detector may also include an interference detector specially designed to detect continuous interference, especially at any of the various mains frequencies of power distribution (e.g. 16–400 Hz) so that false sensing is avoided. In an alternative embodiment a second sense amplifier may be provided having a bandpass in the range of expected power field variations in various frequencies of power distribution (e.g. 16–400 Hz). At every cycle the presence of interference is detected. The time interval between two detections is measured and if this time interval corresponds to any of the main frequencies of power distribution which is preprogrammed, then this detection is labeled as interference and the detection on the other amplifier will be simultaneously labeled also as interference detection and not as a valid slow wave.

The band pass amplifier in the detection circuit 41 should be blanked for a period after a sensed event has been received by the microprocessor 46 or just before and during a stimulation pulse is emitted by output stage discussed below. Blanking may be accomplished through either a blanking switch which disconnects the amplifier from the electrodes or through a program performed in the microprocessor. The microprocessor 46 should also ignore sensed output signals during a period after a sensed or paced event. This is similar to a blanking circuit where sensed events during a blanking period do not affect the timing of the pulse generator. In the preferred embodiment, the blanking period for slow wave detection is on the order of between 0.5 to 4.0 seconds.

Generally speaking, the blanking period decreases with increasing slow wave frequency. The blanking period atgorithm is controlled by the microprocessor. The blanking period algorithm operates such that when the slow wave interval is shortened the blanking period is also shortened. This shortening may be performed in any manner, for example, in a linear fashion or in some other more complex monotonous fashion. After the blanking period, during a certain timing window, the microprocessor 46 is able to receive slow wave detection signals, which will not restart the pulse generator timing circuit, but will instead be interpreted as interference by the microprocessor 46. This timing window, interference detection timing window, may be up to seven seconds in duration after the sensed or paced event, preferably it is 100 milliseconds. To be precise, the combined blanking period and interference detection windows are shortened. Shortening may occur in any manner desired, i.e. in a linear fashion between a preset high or a preset low value or along a non-linear manner. The shortening of the combined blanking and interference detection interval will not occur once the combined blanking and interference detection window reaches a programmed value, such as 2.5 s. This combined blanking window may also be programmed to be turned off such that it does not change in response to sensed physiologic signals. In all circumstances, however, the interference detection window remains equal to at least 100 ms. For example, the rationale is that the typical main frequencies of power distribution are 50 Hz, 60 Hz, 400 Hz and 16.33 Hz. The lower harmonic for 1633 Hz is 8 Hz which corresponds to an interval of 125 ms. Of course the exact length of time for each period may be programmed by the physician. Moreover, each of the periods may be further made to be automatically adjusted based on the sensed electrical activity.

As seen in FIG. 4, blanking switch 42 couples sensing electrodes 4 to amplifier 45 to detect high frequency spike activity. The operation of blanking switch 42 causes the amplifier 45 to be connected to the sensing electrodes 4 once an intrinsic deflection or slow wave has been detected by slow wave detection circuit 41 or a stimulus has been emitted by output stage 47. Preferably, this occurs after a short delay. Blanking switch 42 is closed between 0.5 to 2 seconds after these events and opens roughly 5 to 7 seconds later or at approximately 30% of the intrinsic event interval. As seen, the switch is controlled via the line 46e–42e.

The detection circuit for the high frequency spike activity detector consists of a bandpass amplifier having the center frequency at approximately 300 Hz. As discussed above, however, the center frequency will vary for different organs. The amplifier is followed by two threshold detectors, the first detector detects peak to peak amplitude while the second detector detects slew rate. Both detectors are coupled using a logical AND configuration. The detector pulses are counted, and the interval between pulses is measured. If the interval corresponds to the intervals of the mains frequencies of power distribution or any of their harmonics, i.e. 20 ms or 10 ms, they are rejected. If the number of pulses exceeds a pre-programmed value, then a contraction is indicated. The counter is provided to store in the memory the time of occurrence of the contraction. The number of pulses corresponding to each contraction may be counted and tallied to determine the strength of the contractions. In the present embodiment 3–5 pulses correspond to a weak contraction; 6–8 pulses correspond to a moderate contraction; 9 or more pulses correspond to a strong contraction. Each of these values, of course, may be programmed and the exact number of pulses will vary due to the implementation.

Also coupled to the sensing electrodes 4 is an AC current generator 43. This AC current generator 43 is part of a plethysmorgraphy circuit. Overall, the plethysmography circuit is present to provide a means for sensing mechanical activity of the underlying tissue. That is, whereas the spike activity in the electrogastrogram may be used to sense contraction, the contraction may also be sensed using the plethysmography circuit. Plethsmography circuit is comprised from AC current generator 43, amplifier, modulator and ADC converter 44 as well as a portion of the microprocessor 46. The AC current generator 43 is switched on via signal from microprocessor 46 once a slow wave is detected or a pacing stimulus is emitted. It is switched off roughly 10 seconds after being switched on also from the same line or signal from the microprocessor 46. The AC current generator 43 amplitude and frequency are programmable via microprocessor 46. The frequency should be such it is not detected by amplifiers 41, 45, e.g., 1 kHz. If synchronous detection by amplifier 41 occurs at the end of the blanking period, then the amplitude and/or the frequency of the AC current generator 43 is adjusted by the microprocessor 46 to avoid subsequent detection of the generated AC current.

Turning now to the amplifier, the modulator and ADC converter 44, the AC voltage caused by the injection of AC current generator 43 is amplified and demodulated and converted in order to detect impedance changes caused by contractions of the underlying tissue. The ADC converter digitizes the amplitude of the demodulated signal. The digitized signal is transmitted via line 44c–46h to the microprocessor 46. The microprocessor 46 analyzes the signal pattern by comparing it with one or more templates to identify it as a contraction as well as to reject interference or signals generated by postural changes or vomiting. This template comparison is done synchronously to the detection of the slow wave. Line 46i–44d is used to control the amplifier and ADC from the microprocessor 46.

The microprocessor 46 handles all timings and data storage of the pulse generator and may be of any suitable design. In the preferred embodiment, a microprocessor 46 such as that used in the Thera I series of Medtronic pacemakers is used. The description of the microprocessor 46 function is described in the section below which details the operation of the algorithm used in the present invention.

Stimulation pulses are generated by the output stage 47. In the preferred embodiment, the output stage 47 generates pulse trains. It should be understood many types of pulse trains or stimulation pulses may be used including constant current or constant voltage outputs, or a mixture of both. The output pulses are transported to the gastrointestinal tissue via medical electrical leads 5 and thus to the stomach.

Turning again to the output stage 47, when an output pulse is to be delivered, its amplitude, pulse width and duration and frequencies are controlled via lines 46j–47a. If it is a burst of stimuli, the frequency and duration are controlled through the same line while a burst finished signal is sent to the microprocessor 46 via output line 47b–46k.

Programmability to the pulse generator 3 is achieved through receiver-demodulator 48 and transmitter 49. As seen, each of these devices is coupled to the microprocessor 46. The receiver-demodulator 48 and transmitter 49 are similar to those used in cardiac pacemakers.

The basic parameter settings such as sensitivity (peak voltage or slew rate), refractory, blanking, output pulse amplitude, pulse width, escape interval and ratio, escape interval to a stimulation interval, are stored in the memory of the microprocessor 46. Default values are also stored. These values can be read from memory and sent to a receiver via the transmitter.

Figure 5:
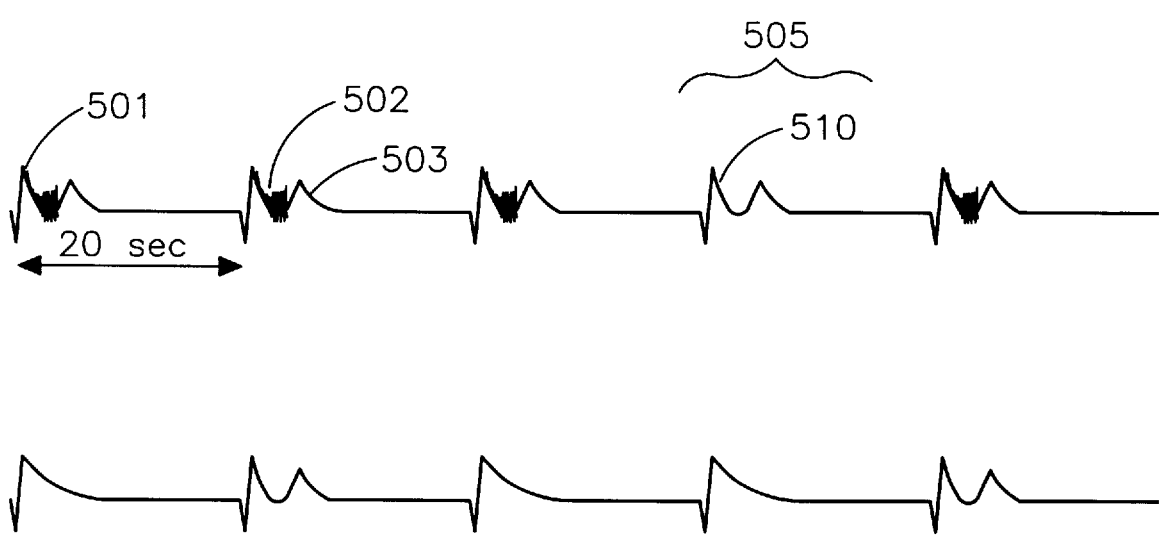
FIG. 5 is an electrogastrogram of the gastrointestinal system.

FIG. 5 shows an electrogastrogram of the stomach in a human. As seen, this intrinsic gastroelectric activity has two distinct components. The first component 501 is a low-frequency, rhythmic depolarization termed slow waves. Superimposed on the slow wave is a high frequency spike activity 502 which corresponds to mechanical contractions of the organ. In the human stomach slow waves are regular, omnipresent depolarizations at 3 cycles/min. (0.05 Hz) that commence high on the greater curvature of the stomach, in the region referred to as the pacemaker region, and propagate aborally, as depicted in FIG. 2.

The normal frequency range for the slow wave in the stomach is between 2.7–3.4 bpm. In clinical situations this value may vary anywhere between 1–15 bpm. High frequency slow wave activity (called tachygastria) does not permit contraction of the stomach readily and may even results in a gastroparesis. In the presence of excessively slow or even absent slow waves (called bradygastria) motility is reduced.

Slow waves and the corresponding spike activity may become irregular or uncoupled or both, thereby-preventing the appearance or organization of regular, normally propagated contractions that constitute normal motility. Contractions cannot occur without gastric electrical response activity which is in turn regulated by the electrical control activity. Any disruption in this delicate sequential order may lead to delayed gastric emptying. An example of such an occurrence is shown in complex 505.

The spike activity occurs incidentally for a few of the slow waves while the patient is in a fasting or non-eating condition. This is termed Migratory Motor Complex phase I. Immediately prior to a meal, typically 30 mins, MMC I changes into MMC II. During this phase the number of slow waves having spike activity increases. Once the meal or eating has begun and up to 120 mins after the meal each further slow wave also has a spike activity component. This condition is called MMC III.

As seen in this complex a slow wave 510 occurs which is not followed by any high frequency spike activity. The absence of such activity indicates there is no longer any peristaltic contraction which will occurs, i.e. gastric emptying is delayed.

FIG. 6 depicts EGG tracings of a stomach illustrating the operation of the device to treat an arrhythmia of the electrogastric activity. As seen, the stomach typically has periodic slow waves which occur at an intrinsic rate of 3 beats per minute or approximately 20 seconds apart. These intrinsic slow waves typically occur at a relatively fixed, periodic rate. Here, these fixed, periodic slow waves are shown as waves 501, 502, 503 and 504, thereby defining intervals 1, 2, and 3.

As seen at interval 4, 5 and 6, however, the slow wave rate decreases or the intervals increase. Thus, waves 505, 506 and 507 occur at ever increasing amounts of time following the prior slow wave. Such a condition is bradygastria and manifests itself in the patient as delayed or inhibited gastric emptying. Of course, the opposite condition, tachygastria which manifests itself in the patient as nausea or vomiting may also be treated with the present invention.

As discussed above, the apparatus of the present invention provides fixed rate stimuli at a higher than intrinsic frequency. This high frequency electrical stimulation is depicted in the figure as the smaller waveforms within the corresponding labeled intervals, that is, within interval 1 stimulation is shown as waves 501-1 and within interval 2 stimulation is shown as waves 502-2, etc.

As seen in this tracing, because the intrinsic slow wave intervals lengthen during intervals 4, 5 and interval 6, the algorithm provides increased frequency of the electrical stimulation in interval 7. As seen, electrical stimulation 507-7 occurs at a smaller interval or thus, higher frequency than that of the preceding intervals. Namely, electrical stimulations 507-7 occur at a rate of 18 beats per minute, or roughly every 3.3 seconds as opposed to the prior rate electrical stimulations of 12 beats per minute or every 5 seconds. As seen, the increased rate of electrical stimulation continues during intervals 7, 8 , 9 and 10.

Figure 6A:
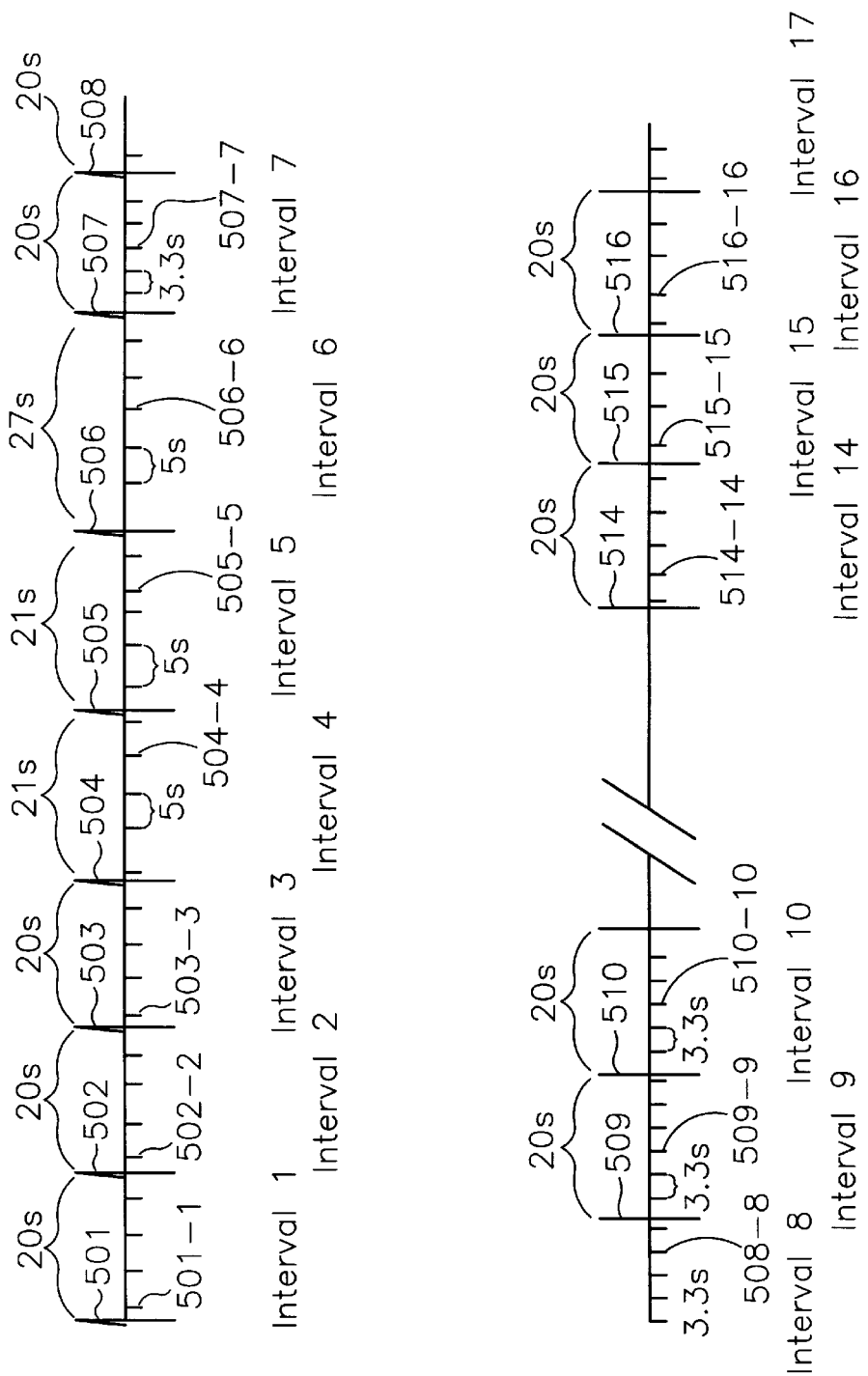
FIGS. 6a and 6b are electrogastrograms illustrating arrhythmias and the response of the apparatus.

FIG. 6A. shows the increased rate of stimulation resulted in an increase or normalization of the slow wave frequency; the intervals 507, 508, 509 and 510 are at 3 bpm. If a number of intervals are within the normal range, the stimulation rate decreases, for example, back to 12 bpm as shown in intervals 514, 515 and 516.

Figure 6B:

FIG. 6B shows, at the normal intervals 8, 9 and 10, stimulation at 18 bpm. Interval 11 shortens and the shortening continues in the intervals 12 and 13. In these intervals gastric stimulation to treat this tachygastria is given and as seen the slow wave regularizes. As seen in interval 14 gastric stimulation returns to the normal mode, for example, 12 bpm. In such a manner the present invention provides a method for treating excessively fast gastric rhythms or tachygastria to thereby regularize slow waves and diminish the symptoms experienced by the patient. It should be noted that as depicted in these figures the delivery of electrical stimulation does not evoke a simulates response in the stomach.

Figure 7:
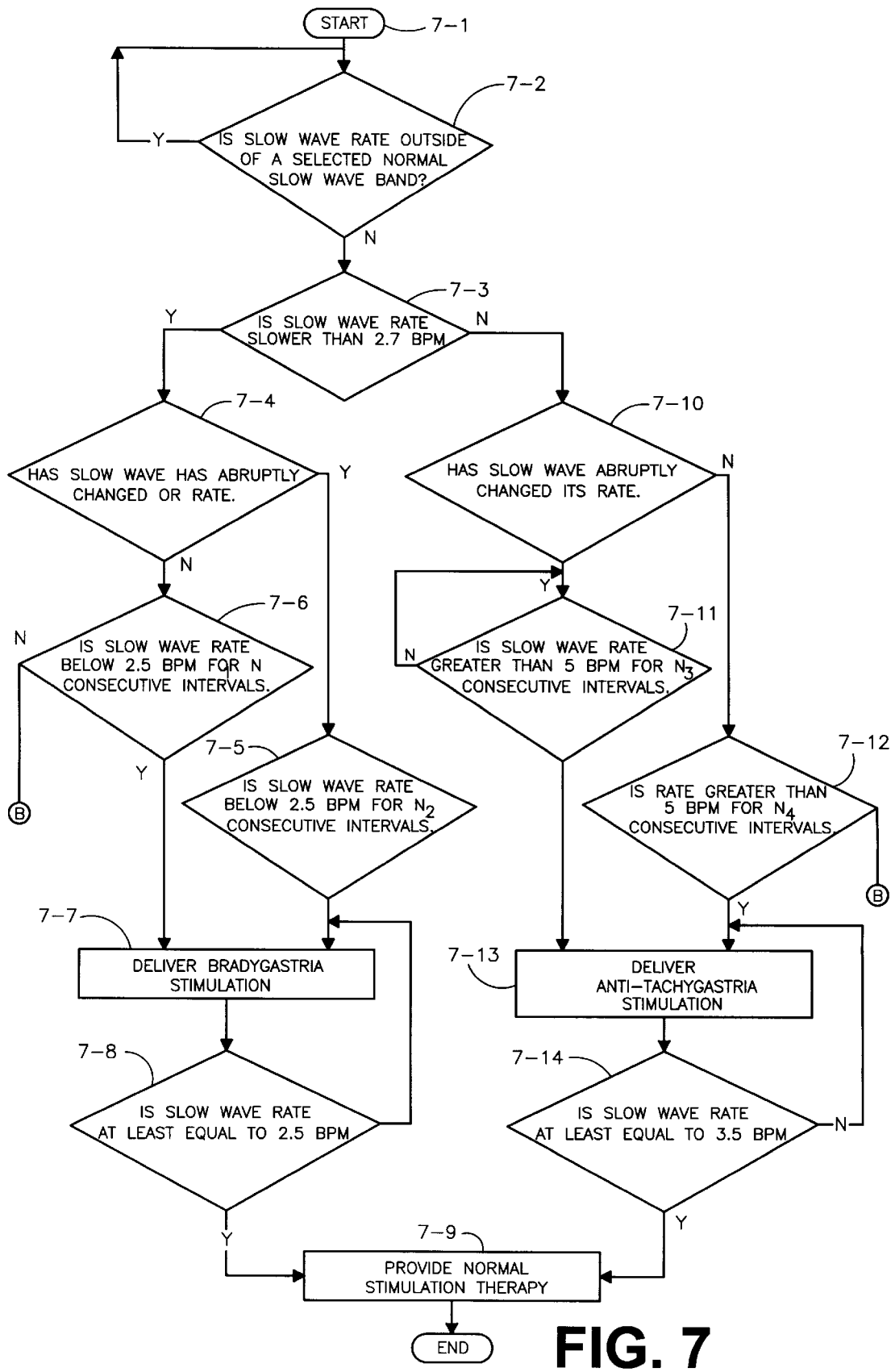
FIG. 7 is a flowchart depicting the operation of the system.

FIG. 7 is a flowchart of the operation of the present system. FIG. 7 depicts the step used in the present invention to normalize slow waves. As discussed above, slow waves occurring outside of a normal frequency (e.g. 3 bpm for the stomach) give rise to nausea or vomiting, or both. Thus the present invention senses whether slow waves are occurring outside of a programmed range and delivers electrical stimulation to thereby normalize slow waves thus treat the symptoms.

As seen, operation starts at step 7-1 and proceeds to step 7-2 where it is determined whether or not the slow wave rate is outside of a selected normal slow wave band. In the preferred embodiment for treating the stomach, step 7-2 comprises sensing whether the slow wave rate is 3 bpm±10%. Thus in step 7-2, in the preferred embodiment, the device senses whether or not the slow wave rate is occurring outside of the range of 2.7 to 3.3 bpm. Of course, the exact slow wave rate is programmable and the bandwidth of detection will depend on the organ being treated, the patient, as well as the preference of the attending physician. As seen, if the slow wave rate is within the selected band, then the device resets itself and again enters step 7-2. If the sensed slow wave rate is outside of this band, then the device proceeds to step 7-3 where it determined whether or not the sensed slow wave rate is slower than 2.7 bpm. Of course, this figure is programmable and depends upon the circumstances. As seen, if the slow wave rate is below 2.7 bpm, the device proceeds to step 7-4. In this step the device senses whether or not the slow wave has abruptly changed its frequency or rate. In the preferred embodiment the device does this by measuring whether a change in the first interval of the slow wave rate is greater than 3 secs. Such a change in the slow wave interval would indicate an abrupt change and the device would proceed to step 7-5. Of course, the number selected may be programmable and would depend upon the circumstances of the usage of the device. As seen in step 7-5, the device determines whether or not the slow wave rate is below 2.5 bpm for $N_2$ consecutive intervals. $N_2$ is a programmable number and in the preferred embodiment is 5. If such a rate is not sensed the device resets itself again and proceeds again through step 7-5. If, however, the slow wave rate is below 2.5 bpm for $N_2$ consecutive intervals, then the device proceeds to step 7-7 and delivers bradygastria stimulation. Bradygastria stimulation used in step 7-7 is shown in detail in FIG. 9, discussed below. If the slow wave rate change was not abrupt as determined in step 7-4, then the device would instead proceed to step 7-6 where it would determine whether or not the slow wave rate is below 2.5 bpm for $N_1$ consecutive intervals. Like $N_2$, $N_1$ is also programmable and in the preferred embodiment is 8. If the rate is not below 2.5 bpm then the device resets itself and again proceeds to step 7-2. If, however, the rate is below 2.5 bpm the device proceeds to step 7-7 and delivers bradygastria stimulation. Once such stimulation has been delivered the device proceeds to step 7-8 and determines whether or not the intrinsic slow wave rate is at least equal to 2.5 bpm. Like each of the parameters described, this number may also be programmed and would depend upon the circumstances of the device used. As seen, if the intrinsic slow wave rate is below 2.5 bpm, the device again enters the above step 7-7 and would again deliver bradygastria stimulation. Sensing intrinsic slow wave rates in step 7-8 may occur in any manner desired, such as temporarily ceasing the electrical stimulation for a preset period of time, e.g. a period of 2 mins, and determining the intrinsic slow wave rate. Of course, greater or less periods of time may be used for determining the slow wave rate. The exact time will, of course, depend upon the circumstances of the usage of the device. As seen, if the intrinsic slow wave rate is equal to or greater than 2.5 bpm, then the device proceeds to step 7-9 and provides normal stimulation therapy. In the preferred embodiment normal stimulation therapy may be either an inhibition mode or a demand mode, i.e. providing electrical stimulation only upon the absence of intrinsic slow wave as detected by the device, or providing electrical stimulation when a demand for such stimulation is sensed by the device.

If bradygastria was not diagnosed in step 7-3, then the device proceeds to step 7-10 to detect and deliver tachygastria. As seen in step 7-10, the device determines whether or not the change in a first interval of the slow wave is greater than 3 secs, i.e. in step 7-10 the device determines whether or not the change in the slow wave interval is abrupt, similar to that of step 7-4. If the change is abrupt then the device proceeds to step 7-12 and the device determines whether or not the rate is greater than 5 bpm for $N_4$ consecutive intervals. Of course, the threshold rate of this step, as well as the number of $N_4$ consecutive intervals, may be programmed. If the rate is not above 5 bpm, then the device resets itself and proceeds to above step 7-2 to begin again. If, however, the sensed slow wave rate is above this value, then the device proceeds to step 7-13 and delivers anti-tachygastria stimulation. If, in step 7-10 an abrupt change was not sensed then the device would have proceeded to step 7-11. In step 7-11 the device determines whether the sensed slow wave rate is greater than 5 bpm for $N_3$ consecutive intervals, of course the exact number of intervals is programmable. Of course, each of these numbers are programmable. If this criteria is not met, the device resets block 7-11 and senses again until step 7-11. If, however, the rate is above 5 bpm for $N_3$ consecutive intervals in step 7-11, then the device proceeds to step 7-13 and delivers anti-tachygastria stimulation. Anti-tachygastria stimulation is described below with regards to FIG. 10. Once such stimulation has been delivered the device moves down to step 7-14 and determined whether the rate is below 3.5 bpm. If not, then the device proceeds again to step 7-13 and again delivers anti-tachygastria stimulation. If the sensed slow wave rate is less than 3.5 bpm, the device proceeds down to step 7-9 and delivers normal stimulation as previously described.

Figure 8:
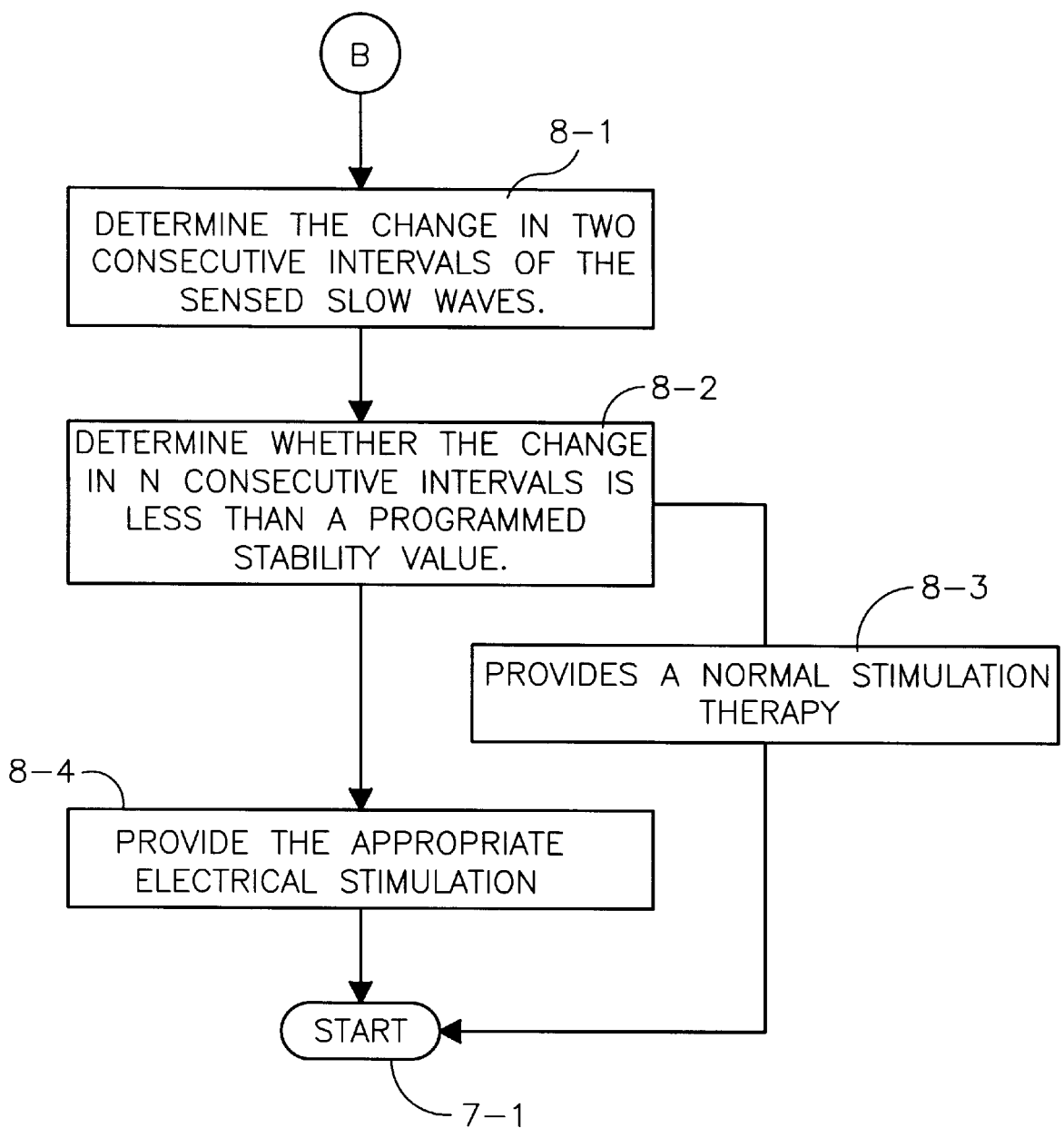
FIG. 8 depicts the steps used in the stability criteria algorithm of the invention.

FIG. 8 depicts the steps used in the stability criteria algorithm of the invention, i.e. the methodology through which the present invention determines whether or not the sensed slow wave rate of the GI tract is, to a sufficient degree, regular. As discussed above, chaotic slow waves which occur at chaotic intervals in time instead of in a normal rhythm may cause the symptoms of nausea or vomiting to occur in a patient. Thus the stability criteria rhythm permits the present invention to sense whether slow waves are occurring in a consistent fashion so that treatment may be delivered should they not occur in such a manner. As seen in step 8-1, the device determines the change in two consecutive intervals of the sensed slow waves. Next, the device proceeds to step 8-2 and adds the absolute values over N consecutive intervals from step 8-1 and determines it is less than a programmed stability value. If the change is less then the device proceeds to step 8-3 and provides a normal electrical stimulation. Step 8-3 corresponds to step 7-9 discussed above. If the value in step 8-2 is not less than the stability value, then the device has detected unstable slow waves and proceeds to step 8-4 to provide the appropriate electrical stimulation. In the preferred embodiment the stimulation delivered in step 8-4 consists of stimulation of between 1.05–1.35 times the sensed slow wave rate or 2–7 times the slow wave rate. Of course, each of these values may be programmed depending upon the circumstances of use of the device, the patient, organ and preference of the attending physician.

Figure 9:
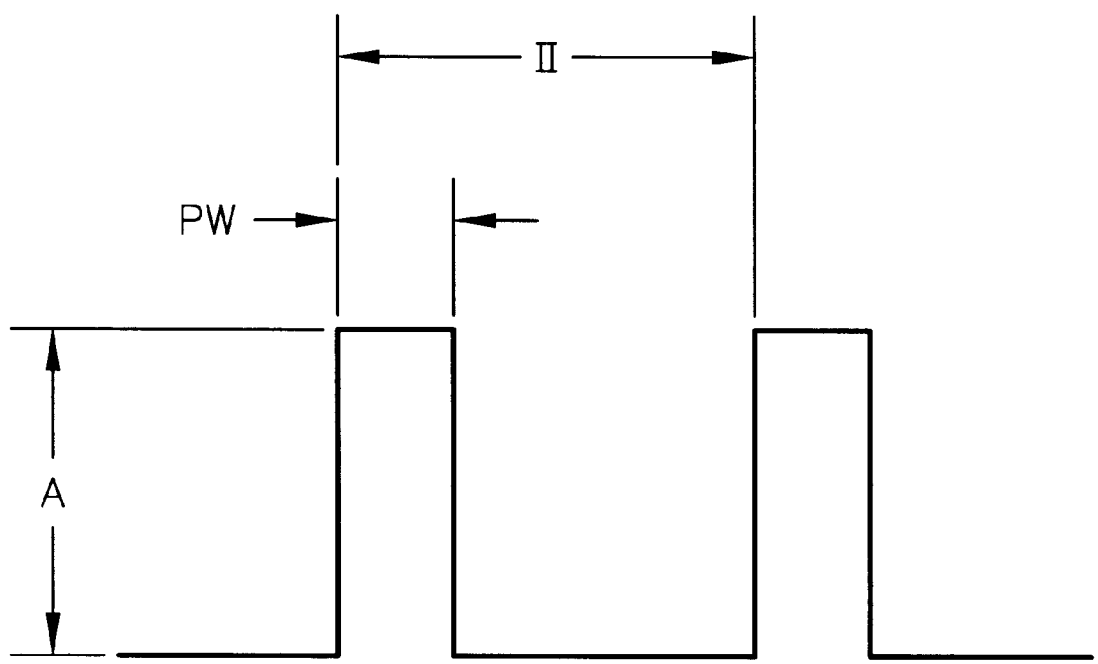
FIG. 9 depicts the electrical stimulation delivered in the normal mode of the device.

FIG. 9 depicts the electrical stimulation delivered in the normal mode of the device. Electrical stimulation preferably consists of a pulse train delivered at a rate of between 7–27 bpm with 12 bpm preferred. As seen, the pulse train preferred consists of two pulses, the pulse having an amplitude A, a pulse width PW and an inter pulse interval II. II may be anywhere between 6–600 ms in length with 60 ms preferred, A is between 1–50 milliamps with 5 milliamps preferred and pulse width is between 3–1000 microsecs with 330 microsecs preferred. Moreover, although the pulse train consisting of two pulses is preferred, any number of pulses between 1–100 may be used. As discussed above, the exact parameters selected depend not only on the organ to be stimulated but also upon the patient's physiology as well as on the preference of the physician attending.

Figure 10:
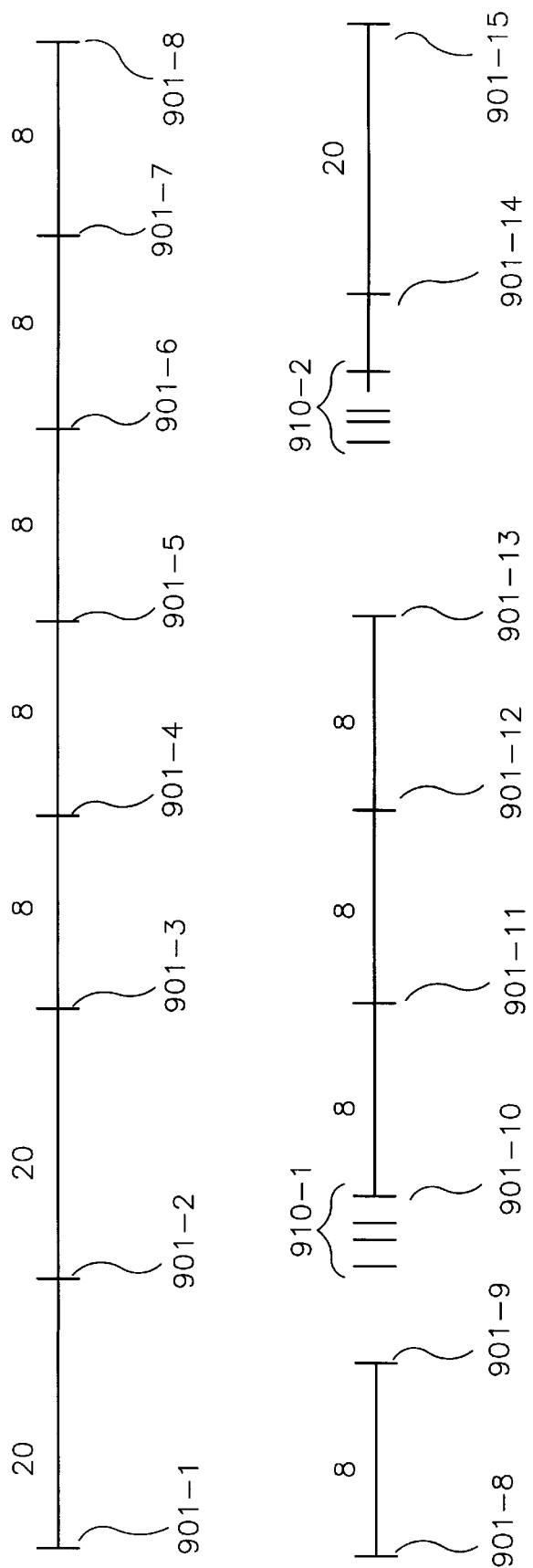
FIG. 10 depicts a series of slow waves in a typical EGG having.

FIG. 10 describes a method of treating tachygastria. As discussed above, one difficulty in properly managing gastric rhythms is the detection and treatment of gastric arrhythmias. One particular type of arrhythmia which causes patient discomfort is the tachyarrhythmia, i.e. excessively fast rates of flow wave depolarizations in the gastricintestinal tract. This may cause nausea or vomiting in those patients. A solution to the proper detection and treatment of such a tachyarrhythmia is to provide a continuous sensing of the slow wave interval. Thus, when the slow wave interval drops below a preset value believed to indicate tachyarrhythmias are occurring, the proper electrical stimulation may be delivered.

As seen in FIG. 10 a typical EGG has a series of slow waves, 901-1 ET SEQ. As seen, between 901-1–901-3 the typical slow wave interval lasts approximately 20 seconds. Upon slow wave 901-4 the slow wave interval has decreased. Upon further slow waves indicative of tachygastria (901-4 through 901-9) tachygastria treatment is triggered and the device provides electrical stimulation at a rate greater than the previously sensed intrinsic rate In particular electrical stimulation is given as a series of pulse trains 910-1 greater than the previously sensed slow wave intervals (discussed below). Such stimulation will entrain the gastrointestinal tissues thereby terminating the gastric arrhythmias. The patients symptoms should then diminish and gastric emptying will increase. In the preferred embodiment this series of electrical stimulation consists of a set of pulse trains delivered at a rate greater than the previously sensed slow wave intervals but which decrements over time. Thus, as seen in the preferred embodiment, a pulse is delivered at 60% of the tachygastria interval. This pulse is coupled to the slow wave. It could be followed, depending on the program, by a second pulse which has a coupling interval of 15% of the tachygastria rate or interval. It could also gain, depending on the physician's preference, followed by a third pulse coupled at 15% of the tachygastria interval. The first tachygastria treatment 910-1 is unsuccessful as a tachygastria continues in intervals 901-11, -12 and -13. A second tachygastria treatment is given at 910-2 which is successful as the slow wave interval 901-14 is prolonged and the slow wave interval 901-15 is normal. Thus, as seen, the present invention provides electrical stimulation to treat and thereby correct tachygastria. In such a way the tachygastria is captured and eventually slows. It should be noted, however, that through such stimulation the organ is not entrained or captures as is well known in the field of cardiac stimulation. In fact as seen upon a close examination of this fig, the various pulse trains 910-2 et seq. do not result in an immediate and corresponding depolarization in the EGG, e.g. 901-6 et seq. Of course, an alternative method to treat tachygastria is stimulation at a 5 to 30% higher or slower rate than the tachygastria, while also monitoring if the tachygastria has terminated, at which time the device returns to normal operation.

Figure 11:
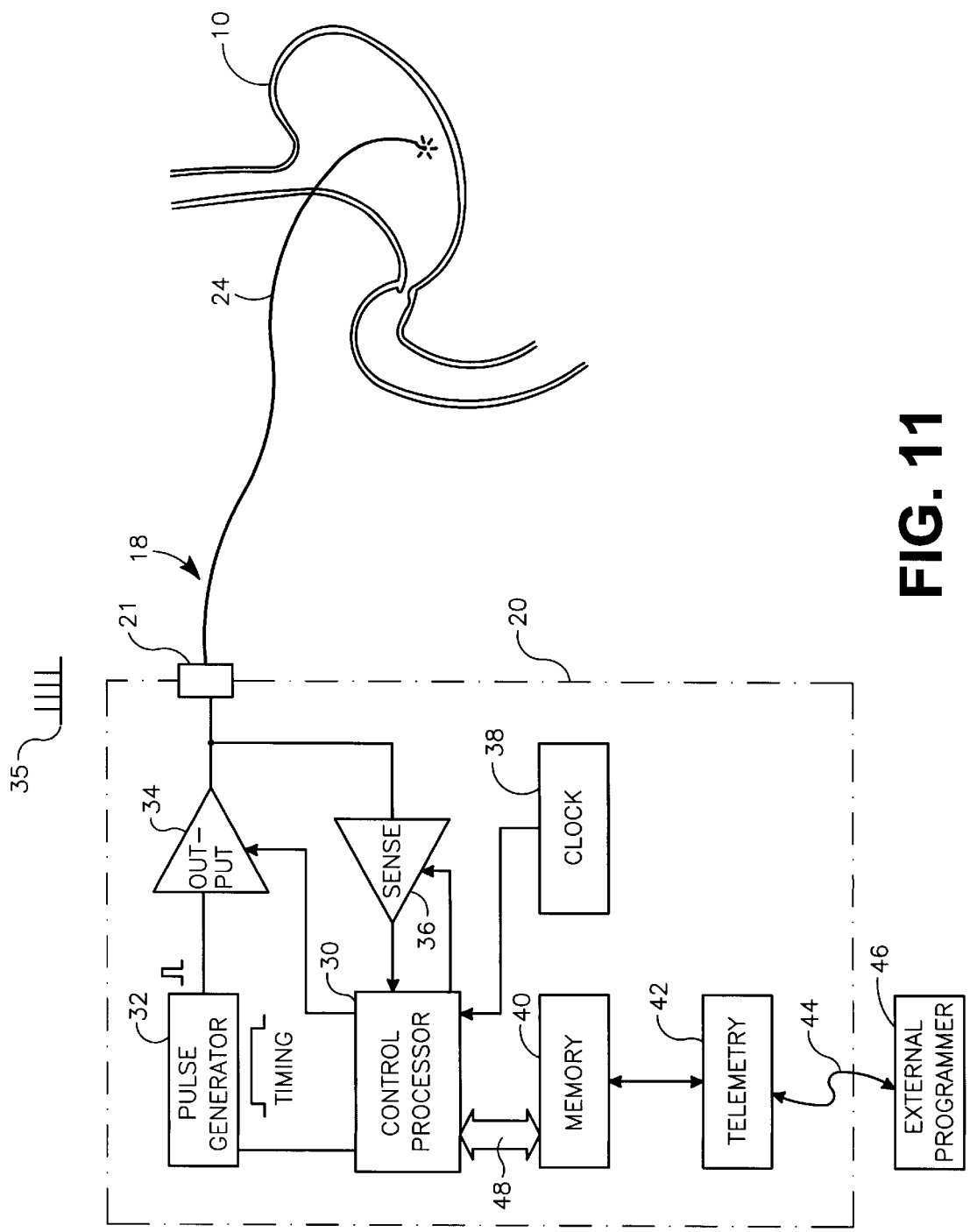
FIG. 11 shows a block diagram of an alternate embodiment of the present invention.

Referring first to FIG. 11, there is shown a functional block diagram of an alternate embodiment of a gastrointestinal stimulation system 18 made in accordance with the present invention. The gastrointestinal stimulation system 18 includes an implantable stimulator 20 which is used in conjunction with an external programmer 46. The stimulator 20 includes an output connector 21 through which one or more medical electrical leads 24 may be connected to the internal circuits of the stimulator. The lead 24 is typically the Medtronic model 4300 intramuscular lead. FIG. 11 shows a single lead 24 being used to couple the stimulator 20 to the GI tract, however, it is to be understood that the use of a single lead in this manner is only exemplary, as the invention may be used equally well with systems that include multiple leads that make contact with multiple locations within the GI tract or other body tissue locations.

The internal circuits of the stimulator with which the lead 24 makes contact when inserted into the connector 21 include an output amplifier 34 and a sense amplifier 36. The output amplifier 34 generates an electrical stimulation pulses 35 as controlled by a pulse generator 32. The pulse generator 32, in turn, receives timing signals from a control processor 30. Such timing signals control when the stimulation pulses 35 are to be generated.

The sense amplifier 36 monitors the electrical signals appearing on the lead 24, and processes such signals. Such processing typically includes amplification, filtering, and threshold detection. If a valid depolarization signal ("intrinsic event") is sensed by the sense amplifier 36, then the sense amplifier provides an appropriate signal to the control processor 30 of such sensed intrinsic event. If no valid intrinsic events are sensed during a prescribed time period, referred to generally as the "escape interval," then the control processor 30 signals the pulse generator to generate a stimulation pulse. If a valid intrinsic event is sensed before the escape interval times out, the control processor responds by resetting the escape interval, thereby preventing the pulse generator from generating a stimulation pulse. In this manner, the stimulator 20 provides stimulation pulses only when needed, e.g., only when a valid intrinsic event is not sensed.

A clock circuit 38 provides the necessary clock signals for operation of the control processor 30. The control processor 30, which may be a microprocessor or equivalent processing circuit, operates in accordance with a control program that is stored in the stimulator memory 40. Also stored in the memory 40 is a set of control parameters that are used by the control program as it defines the operation of the processor 30. That is, the control parameters define the various variables associated with the operation of the stimulator, such as the duration of the escape interval, the frequency, interpulse interval, duration and amplitude of the stimulation pulses and the like. The control program specifies the particular order or sequence of events that are carried out by the processor 30. For example, the control program may specify that, upon detecting a valid intrinsic event, a control parameter stored in a particular address in the memory 40 should be retrieved in order to define an appropriate corresponding delay. The control program may further specify that if a further valid intrinsic event is sensed before the delay times out, then another control parameter stored in another location (address) of the memory 40 should be retrieved in order to define an appropriate delay. If a valid intrinsic event is not sensed before the timing out of the delay, then the control program may specify another memory address where a control parameter is stored that defines the amplitude and pulse width of a stimulation pulse train that is to be generated.

Of course, the above example is extremely simple, but it illustrates the basic operation of the stimulator 20. Those skilled in the art will recognize that there are numerous events associated with the gastrointestinal cycle, and that there are numerous types of cycles that may occur. The control program, in combination with the other control circuitry within the stimulator, thus define how the stimulator responds to each possible event and intrinsic cycle type. The control parameters, in turn, define the magnitude of the variables associated with such response, e.g., the duration of time periods, the amplitude and widths of stimulation pulses, the gain of amplifiers, the threshold level of threshold detectors, and the like.

In order to add flexibility to the operation of the stimulator 20, the stimulator also includes a telemetry circuit 42. The telemetry circuit 42 allows access to the memory 40 from a remote location, e.g., from an external programmer 46 at a nonimplanted location. The external programmer 46 includes means for establishing a telemetry link 44 with the telemetry circuit 42 of the implanted stimulator. Through this telemetry link 44, control parameters may be sent to the telemetry circuit 42 for storage in the memory 40. Such control parameters may thereafter be used by the control program stored in the memory 40 to steer the operation of the stimulator 20, as explained above. Additional details associated with the design and operation of a telemetry circuit 42, as well as an external programmer 46, may be found in U.S. Pat. Nos. 4,809,697 and 4,944,299, which patents are incorporated herein by reference.

In operation, the external programmer 46 is used to programmably set the control parameters associated with operation of the control processor 30. However, heretofore, the external programmer 46 has not ever been used to alter or change the control program once the stimulator has been implanted in a patient. Rather, the control program is downloaded to the memory 40 during the manufacture of the stimulator 20. In some instances, the control program is stored in read only memory (ROM), or equivalent hardwired circuitry, so that it can never to updated or changed thereafter. In other instances, it is stored in random access memory (RAM), but access to it is denied. This is done purposefully to preserve the integrity of the control program, or stated more accurately, to preserve the integrity of the function(s) controlled by the control program as well as providing the greatest amount of flexibility to permit changing of the device operation.

In contrast to the control program, which preferably is fixed, certain control parameters that define the variables used by the control program (or equivalent circuitry) in controlling the stimulator may be readily changed, from time to time, after implantation by using the external programmer 46. Thus, should there be a need to change a given control parameter, e.g., the stimulation pulse amplitude generated by the output amplifier 34, the sensitivity (threshold setting) of the sense amplifier 36, or other variables, then the appropriate control parameters that define such variables are simply updated (programmed) through the telemetry link established by the external programmer 46. Such programming of the control parameters is limited, however, so that the associated variables can only be changed within certain safe limits that are defined by the control program and/or other circuitry within the stimulator.

The memory 40 is a RAM memory that has both a control program and a set of control parameters stored therein at respective memory locations (addresses). Like conventional programmable stimulators, the set of control parameters in the memory 40 may be selectively updated (programmed), as needed, through use of the external programmer 46. The control program stored in the memory 40 may also be updated, using appropriate safeguards, through use of the external programmer 46. Thus, when new features requiring a new control program are added to the stimulator, a patient having an existing implanted stimulator can receive the benefits of such new features by simply upgrading the control program stored in his or her implanted stimulator. In this manner, the invention allows an existing control program stored in an implanted stimulator to be non-invasively upgraded to a new version of the control program.

Figure 12:
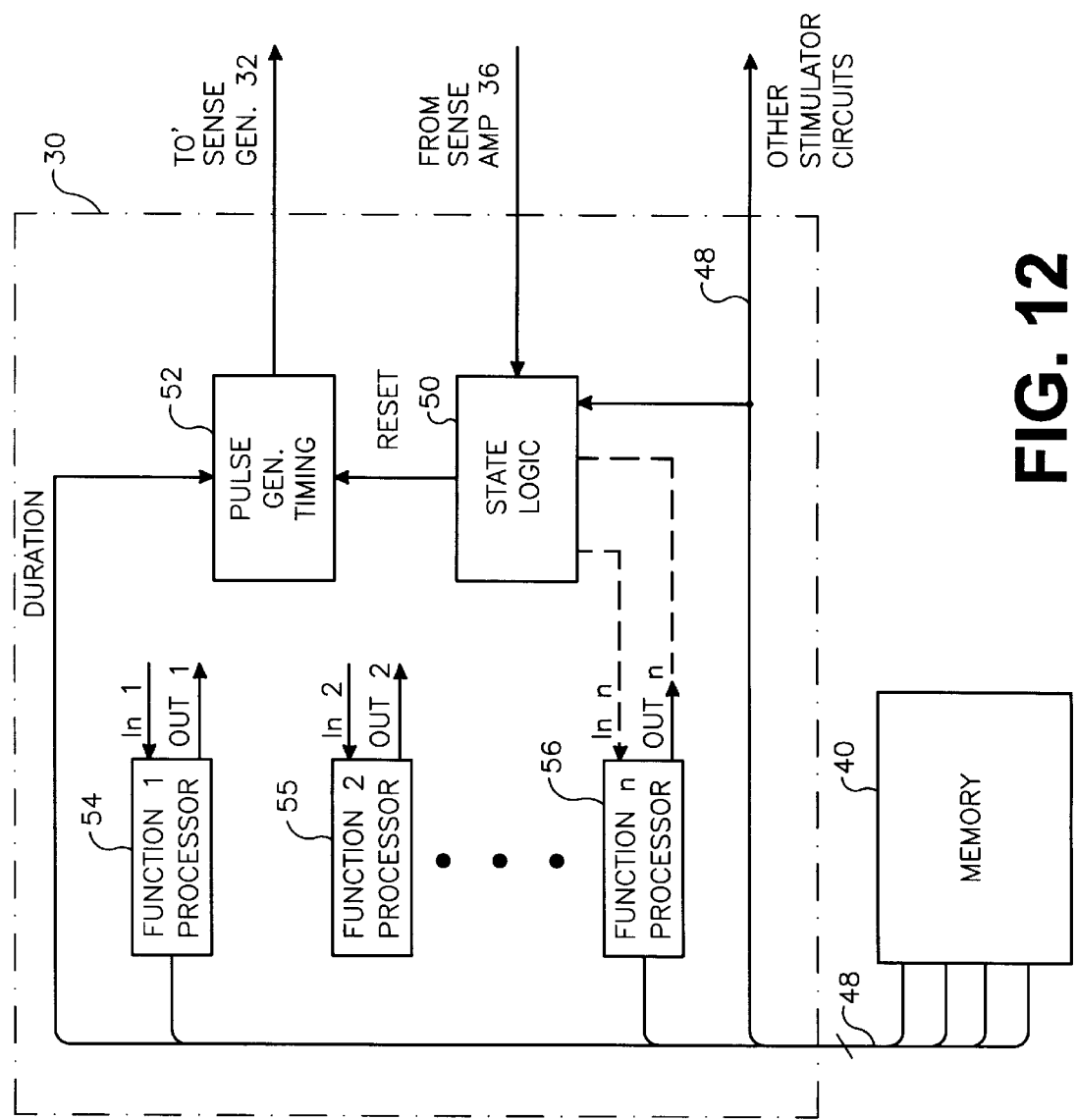
FIG. 12 is a block diagram of one embodiment of the control processor of FIG. 11.

As illustrated in FIG. 12, the control processor 30 may include multiple processors 54, 55 and 56. Each processor 54, 55 and 56 is programmed, using a respective control program stored in the memory 40, to perform a specific function associated with the operation of the stimulator 20. Such functions are supplemental to the main stimulator function, which is to monitor the stomach, or any other organ along the GI tract, 22 for natural intrinsic events, and to provide stimulation pulses in the event that no natural intrinsic events are sensed, in accordance with a prescribed pacer mode. As seen an indefinite number of processors may be provided, the exact number depending upon the number of functions required to be performed.

State logic circuitry 50 carried out the main stimulator function, as well as the prescribed pacer mode function. The state logic circuitry 50 may be considered as a dedicated control circuit for the stimulator 20. The state logic 50 defines the state of the stimulator as a function of the input signals it receives. One such input is from the sense amplifier 36 (which may include inputs from one or all of the leads used, depending upon the particular stimulator configuration enabled). Another set of inputs to the state logic is a set of control parameters obtained from the memory 40 over a data bus 48. The data bus 48 interfaces the memory 40 with the various circuits used within the stimulator. Thus, for example, a set of control parameters defines a particular operating mode for the state logic. Such operating mode dictates the particular sequence followed by the state logic, e.g., whether it operates in an inhibited or triggered mode, asynchronous, etc. Another set of control parameters defines the duration of the timing interval used by pulse generator (PG) timing circuitry 52 in controlling the various time intervals, e.g., escape intervals, used by the stimulator as it carries out its stimulation basic function.

Still other of the control parameters available on the data bus 48 are directed to the appropriate circuits that use such parameters in controlling the operation of the stimulator, e.g., the sensitivity control parameter is directed to the sense amplifier 36; the pulse amplitude and width control parameters are directed to the output amplifier 34; and so on.

The functions carried out by each of the processors 54, 55 and 56 may be varied, depending upon the particular needs of the patient. (It is to be understood that just because three processors 54, 55 and 56 are shown in FIG. 12 as part of the control processor 30, the invention is not so limited. The control processor 30, for the particular embodiment shown in FIG. 12, may include any number of processors, e.g., 1 to 10, that supplement the basic stimulation function carried out by the state logic 50. The functions carried out by the processors 54, 55 and/or 56 may include, e.g., the sensing and processing of a physiological parameters, such as gastric pH. Further, the processors may monitor and report parameters associated with the operation of the stimulator, such as remaining battery life, the time of day, the occurrences of prescribed events (such as tachygastria, bradygastria, vomiting or contractile activity) and the like. Indeed, the processors 54, 55, 56 . . . (however many may be used) may be used for many different types and varied functions associated with the use and operation of an implantable stimulator.

As seen in FIG. 12, the control processor 30 is effectively divided into two portions: (1) a portion that controls the basic stimulation functions, comprising the state logic 50 and the pulse generator (PG) timing circuits 52; and (2) a portion that controls the supplemental stimulation functions, comprising the processors 54, 55, and/or 56. It is to be understood that the first control processor portion, i.e., the portion that controls the basic stimulation function, could be realized using circuitry other than that shown in FIG. 12. For example, a suitable processor circuit, such as a microprocessor circuit, could readily be programmed to perform the basic stimulation function carried out by the state logic 50 and PG timing circuitry 52. Similarly, the functions carried out by the supplemental processors 54, 55 and/or 56 could likewise be achieved using specially designed hardware circuits. Indeed, any configuration of the control processor 30 that provides both supplemental and basic stimulation functions could be utilized, whether such configuration uses conventional processing circuits (e.g., microprocessors) or dedicated logic circuitry (e. g., state logic).

One of the advantages of having the control processor 30 configured as shown in FIG. 12 (to provide both the basic stimulation function and supplemental stimulation functions) is that the control programs for the supplemental stimulation function(s) can be altered (upgraded with a new program) at the same time that the basic stimulation function continues to operate. Thus, there need be no interruption in the basic stimulation function provided by the stimulator as one or more control programs are downloaded to the memory 40. As the downloading operation could take several minutes, this is an important advantage because it means the patient need not go without the therapeutic stimulation pulses provided by the stimulator.

Although a specific embodiment of the invention has been disclosed, this is done for the purposes of illustration and is not intended to be limiting with regard to the scope of the invention. It is contemplated that various substitutions, alterations, and/or modifications, including but not limited to those specifically discussed herein, may be made to the disclosed embodiment of the invention without departing from the spirit and scope of the invention as defined in the appended claims, which follow.

What is claimed is:

1. An apparatus for providing electrical stimulation to the GI tract, comprising:
   a sensor for sensing a first interval of intrinsic gastrointestinal electrical activity between the frequency of 1 to 15 cycles/min. (0.017–0.25 Hz) and a second interval of intrinsic gastrointestinal electrical activity between the frequency of 1 to 15 cycles/min. (0.017–0.25 Hz);
   a signal processor to process the sensed intrinsic gastrointestinal electrical activity and generate an abnormal gastrointestinal electrical activity trigger signal when the first interval differs from the second interval by an abnormal amount;
   a pulse generator, the pulse generator coupled to the signal processor so as to receive the abnormal gastrointestinal electrical activity trigger signal, the pulse generator coupled to at least one medical electrical lead, the pulse generator emitting stimulation pulse trains at a first rate, wherein the first rate is a multiple of an average of a sensed intrinsic gastrointestinal electrical activity rate, and the multiple is about three times the average of a sensed intrinsic gastrointestinal electrical activity rate.

2. The apparatus according to claim 1, wherein the stimulation pulse trains comprise a series of pulse trains emitted at a frequency of 30 Hz and a duration of approximately 4 seconds, each pulse lasting 330 microseconds with an amplitude of between approximately 0.5 to 10 Volts or a current of between approximately 0.1 milliamps to 30 milliamps.

3. The apparatus according to claim 1, wherein the pulse train having a first section and a second section, the first section having a first frequency, the second section having a second frequency.

4. The apparatus of claim 1, wherein the first frequency is greater than the second frequency.

5. The apparatus of claim 1, wherein the first frequency is less than the second frequency.

6. The apparatus of claim 1, wherein the first section has a first amplitude, the second section has a second amplitude.

7. The apparatus of claim 1, wherein the first amplitude is less than the second amplitude.

8. A method of regularizing slow waves in the GI tract comprising the steps of:
   sensing slow wave within the GI tract and determining the a slow wave rate;
   detecting whether the slow wave rate is outside a predetermined normal slow wave band;
   detecting whether the slow wave rate has changed its rate outside a predetermined slow wave rate change band; and
   delivering normalizing gastric rhythm electrical stimulation if the slow wave rate has changed outside a predetermined slow wave rate change band;
   wherein the normalizing gastric rhythm electrical stimulation comprises delivering a series of electrical stimulation pulse trains and the electrical stimulation pulse trains are a series of pulse trains emitted at a frequency of 30 Hz and a duration of approximately 4 seconds, each pulse lasting 330 microseconds with an amplitude of between approximately 0.5 to 10 Volts or a current of between approximately 0.1 milliamps to 30 milliamps.

9. A method of regularizing slow waves in the GI tract according to claim 8, further comprising the steps of determining whether tachygastria is present and delivering tachygastria electrical stimulation, and
   determining whether bradygastria is present and delivering bradygastria electrical stimulation.

10. A method of regularizing slow waves in the GI tract according to claim 9, wherein the step of delivering bradygastria electrical stimulation comprises delivering a series of one or more electrical pulses, each pulse having an amplitude between approximately 1–50 milliamps and pulse width between approximately 3–1000 microsecs.

11. A method of regularizing slow waves in the GI tract according to claim 10, wherein the bradygastria electrical stimulation is delivered at a rate of between approximately 7–27 bpm.

* * * * *

UNITED STATES PATENT AND TRADEMARK OFFICE
CERTIFICATE OF CORRECTION

PATENT NO.   : 6,216,039 B1
DATED        : April 10, 2001
INVENTOR(S)  : Bourgeois It is certified that error appears in the above-identified patent and that said Letters Patent is hereby corrected as shown below:

Column 16,
Lines 26-27, change "the a" to -- the --.

Signed and Sealed this

Twenty-fifth Day of March, 2003

JAMES E. ROGAN
*Director of the United States Patent and Trademark Office*